US012628555B2

(12) United States Patent
Lee et al.

(10) Patent No.: US 12,628,555 B2
(45) Date of Patent: May 12, 2026

(54) COMPOUND AND THIN FILM TRANSISTOR AND ELECTRONIC DEVICE

(71) Applicant: Samsung Electronics Co., Ltd., Suwon-si (KR)

(72) Inventors: Eun Kyung Lee, Seoul (KR); Don-Wook Lee, Seoul (KR); Jeong Il Park, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 948 days.

(21) Appl. No.: 17/882,778

(22) Filed: Aug. 8, 2022

(65) Prior Publication Data

US 2022/0416173 A1 Dec. 29, 2022

Related U.S. Application Data

(62) Division of application No. 16/546,842, filed on Aug. 21, 2019, now Pat. No. 11,450,810.

(30) Foreign Application Priority Data

Aug. 28, 2018 (KR) ........................ 10-2018-0101500

(51) Int. Cl.
*H10K 85/60* (2023.01)
*C07D 495/04* (2006.01)
(Continued)

(52) U.S. Cl.
CPC ......... *H10K 85/657* (2023.02); *C07D 495/04* (2013.01); *C07D 517/04* (2013.01); (Continued)

(58) Field of Classification Search
CPC ............ G02F 1/13439; C09K 2323/04; C07D 495/04; C07D 517/04; H10K 85/6576; H10K 85/657; H10K 10/46
See application file for complete search history.

(56) References Cited

U.S. PATENT DOCUMENTS 7,351,266 B2 4/2008 Glenn, Jr. et al.
7,468,080 B2 12/2008 Glenn, Jr. et al.
(Continued)

FOREIGN PATENT DOCUMENTS

CN 103242360 A 8/2013
CN 103664995 A 3/2014
(Continued)

OTHER PUBLICATIONS

M. Vafai, Bulletin des Societes Chimiques Belges, 75(3-4), 1966, pp. 145-146 (Year: 1966).*
(Continued)

*Primary Examiner* — Sophie Hon
(74) *Attorney, Agent, or Firm* — HARNESS, DICKEY & PIERCE, P.L.C.

(57) ABSTRACT

Disclosed are a compound represented by Chemical Formula 1A or 1B, an organic thin film including the same, a thin film transistor, and an electronic device.

[Chemical Formula 1A]

[Chemical Formula 1B]

(Continued)

In Chemical Formulae 1A and 1B, $X^1$, $X^2$, $R^1$ to $R^4$, and n1 are the same as described in the detailed description.

12 Claims, 5 Drawing Sheets

(51) Int. Cl.
*C07D 517/04* (2006.01)
*G02F 1/1343* (2006.01)
*H10K 10/46* (2023.01)

(52) U.S. Cl.
CPC ......... *G02F 1/13439* (2013.01); *H10K 10/46* (2023.02); *C09K 2323/04* (2020.08); *H10K 10/466* (2023.02); *H10K 10/484* (2023.02)

(56) References Cited

U.S. PATENT DOCUMENTS

| | | | |
|---|---|---|---|
| 7,816,673 B2 | 10/2010 | Park et al. | |
| 9,018,398 B2 | 4/2015 | Takimiya et al. | |
| 9,318,713 B2 | 4/2016 | Park et al. | |
| 9,705,095 B2 | 7/2017 | Youfu et al. | |
| 11,450,810 B2 * | 9/2022 | Lee ...................... | C07D 517/04 |
| 2005/0193504 A1 | 9/2005 | Glenn et al. | |
| 2008/0134450 A1 | 6/2008 | Glenn et al. | |
| 2011/0224445 A1 | 9/2011 | Takimiya | |
| 2013/0161568 A1 | 6/2013 | Wang et al. | |
| 2015/0045560 A1 | 2/2015 | He et al. | |
| 2016/0315271 A1 | 10/2016 | Youfu et al. | |
| 2016/0369045 A1 | 12/2016 | He et al. | |
| 2017/0170399 A1 | 6/2017 | Masui et al. | |
| 2017/0288152 A1 | 10/2017 | Kariya et al. | |

FOREIGN PATENT DOCUMENTS

| | | | |
|---|---|---|---|
| CN | 110862402 B * | 7/2024 | ........... C07D 517/04 |
| EP | 2207218 A1 | 7/2010 | |
| JP | 2005-154371 A | 6/2005 | |
| JP | 2007/067262 A | 3/2007 | |
| JP | 2008/103464 A | 5/2008 | |
| JP | 2008258592 A | 10/2008 | |
| JP | 2010177642 A | 8/2010 | |
| JP | WO 2009/038120 A1 | 1/2011 | |
| JP | 2015/133358 A | 7/2015 | |
| JP | 2015519300 A | 7/2015 | |
| JP | 5840197 B2 | 1/2016 | |
| JP | 6275883 B2 | 2/2018 | |
| JP | 6301488 B2 | 3/2018 | |
| KR | 2007/0089043 A | 8/2007 | |
| KR | 20110075024 A | 7/2011 | |
| KR | 20120078051 A | 7/2012 | |
| KR | 20130103530 A | 9/2013 | |
| KR | 20140123070 A | 10/2014 | |
| KR | 20150056051 A | 5/2015 | |
| KR | 102631401 B1 * | 1/2024 | ........... C07D 517/04 |
| WO | WO-2007125671 A1 | 11/2007 | |
| WO | WO-2012118174 A1 | 9/2012 | |
| WO | WO-2013031468 A1 | 3/2013 | |
| WO | WO-2015/087875 A1 | 6/2015 | |
| WO | WO-2017210072 A1 | 7/2017 | |
| WO | WO-2018097937 A1 | 5/2018 | |

OTHER PUBLICATIONS

P. Maity, Organic Letters, vol. 19, 2017, pp. 5748-5751 (Year: 2017).*

Office Action for Korean Application No. 10-2018-0101500 dated Sep. 22, 2023.

H. Tsuji et al., 'Modular Synthesis and Photophysical and Electrochemical Properties of 2, 3, 5, 6-Tetraaryl-Substituted Benzo [1, 2-b.5, 4-b] difurans' *Heteroatom Chemistry*, vol. 22, No. 3/4, 2011, pp. 316-324.

Partial European Search Report dated Oct. 21, 2019, issued in corresponding European Patent Application No. 19193697.0.

European Office Action dated Sep. 8, 2021, issued in corresponding European Patent Application No. 19 193 697.0.

Pintu Maity et al., 'Transition-Metal-Free Iodine Catalyzed Selenocayanation of Styrenyl Bromides and an Easy Access to Benzoselenophenes via Intermediacy of Styrenyl Selenocyanate' *Organic Letters*, vol. 19, 2017, pp. 5748-5751.

M. Vafai and M. Renson, 'Synthesis of selenopheno[2',3';5,6]benzo[b]thiophene' *Bulletin des Societes Chimiques Belges*, 75(3-4), 1966, pp. 145-156.

Office Action dated Mar. 7, 2023, issued in corresponding Korean Patent Application No. 10-2018-0101500.

* cited by examiner

COMPOUND AND THIN FILM TRANSISTOR AND ELECTRONIC DEVICE

CROSS-REFERENCE TO RELATED APPLICATION

This application is a divisional of U.S. application Ser. No. 16/546,842, filed Aug. 21, 2019, which claims priority to and the benefit of Korean Patent Application No. 10-2018-0101500 filed in the Korean Intellectual Property Office on Aug. 28, 2018, the entire contents of each of which are incorporated herein by reference.

BACKGROUND

1. Field

A compound, a thin film transistor, and an electronic device are disclosed.

2. Description of Related Art

A flat panel display such as a liquid crystal display (LCD) or an organic light emitting diode (OLED) display includes a thin film transistor (TFT) that is a three-terminal element as a switch. Researches on an organic thin film transistor (OTFT) including an organic semiconductor such as a small molecular semiconductor or polymer semiconductor instead of an inorganic semiconductor such as a silicon (Si) semiconductor as one kind of the thin film transistor are being actively conducted.

The organic thin film transistor may be made as a fiber or a film due to characteristics of an organic material, and thus is drawing attention as a core element for a flexible display device. The organic thin film transistor may be manufactured using a solution process such as inkjet printing, and may be easily applied to a large area flat panel display where a deposition process has a limit.

SUMMARY

An embodiment provides a compound applicable to an electronic device such as a thin film transistor.

Another embodiment provides an organic thin film including the compound.

Yet another embodiment provides a thin film transistor including the compound.

Still another embodiment provides an electronic device including the thin film transistor.

According to one embodiment, a compound represented by Chemical Formula 1A or 1B is provided.

[Chemical Formula 1A]

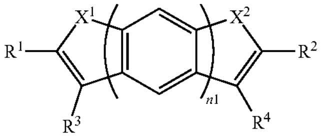

[Chemical Formula 1B]

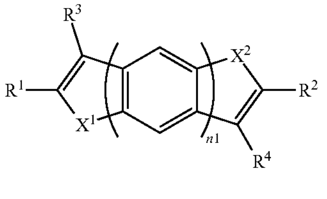

In Chemical Formulae 1A and 1B, $X^1$ and $X^2$ are different from each other and are independently one of O, S, Se, and Te, $R^1$ to $R^4$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is an integer ranging from 1 to 4.

In some embodiments, one of $X^1$ and $X^2$ may be Se or Te.

In some embodiments, one of $X^1$ and X2 may be S.

In some embodiments, $R^1$ and $R^2$ may be different from each other.

In some embodiments, one of $R^1$ and $R^2$ may be hydrogen and the other of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

In some embodiments, one of $R^1$ and $R^2$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^1$ and $R^2$ may be one of a substituted or unsubstituted C1 to C30 branched alkyl group, a substituted or unsubstituted C2 to C30 branched alkenyl group, a substituted or unsubstituted C2 to C30 branched alkynyl group, or a combination thereof.

In some embodiments, one of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be one of a substituted or unsubstituted C6 to C30 aryl group, a substituted or unsubstituted C6 to C30 aryloxy group, a substituted or unsubstituted C3 to C30 heteroaryl group, or a combination thereof.

In some embodiments, one of $R^1$ and $R^2$ may include a group represented by one of Chemical Formulae 2A to 2C.

[Compound 2A]

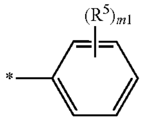

[Compound 2B]

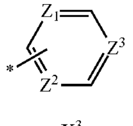

[Compound 2C]

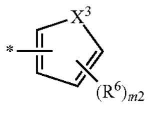

In Chemical Formulae 2A to 2C, $Z^1$ to $Z^3$ may independently be N or $CR^a$, one of $Z^1$ to $Z^3$ may be N, $X^3$ may be one of O, S, Se, Te, $NR^b$, or $CR^cR^d$, m1 may be an integer ranging from 0 to 5, m2 may be an integer ranging from 0 to 3, $R^5$, $R^6$, and $R^a$ to $R^d$ may independently be one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, when m1 is two or more, each $R^5$ may be the same or different and two adjacent $R^5$'s may be independently present or linked with each other to form a ring, and when m2 is two or more, each $R^6$ may be the same or different and two adjacent $R^6$'s may be independently present or linked with each other to form a ring.

In some embodiments, $X^1$ may be O or S, $X^2$ may be Se or Te, one of $R^1$ and $R^2$ may be hydrogen, and the other of R1 and R2 may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

In some embodiments, $X^1$ may be O or S, $X^2$ may be Se or Te, one of $R^1$ and $R^2$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^1$ and $R^2$ may be one of a substituted or unsubstituted C1 to C30 branched alkyl group, a substituted or unsubstituted C2 to C30 branched alkenyl group, a substituted or unsubstituted C2 to C30 branched alkynyl group, or a combination thereof.

In some embodiments, $X^1$ may be O or S, $X^2$ may be Se or Te, one of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be one of a substituted or unsubstituted C6 to C30 aryl group, a substituted or unsubstituted C6 to C30 aryloxy group, a substituted or unsubstituted C3 to C30 heteroaryl group, or a combination thereof.

In some embodiments, $X^1$ may be one of S, Se, and Te. $X^2$ may be one of O, S, Se, and Te.

In some embodiments, one of $R^1$ and $R^2$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof. The other of $R^1$ and $R^2$ may be one of a substituted or unsubstituted C4 to C30 branched alkyl group, a substituted or unsubstituted C4 to C30 branched alkenyl group, a substituted or unsubstituted C4 to C30 branched alkynyl group, or a combination thereof.

In some embodiments, the compound may include a group listed in Group 1:

[Group 1]

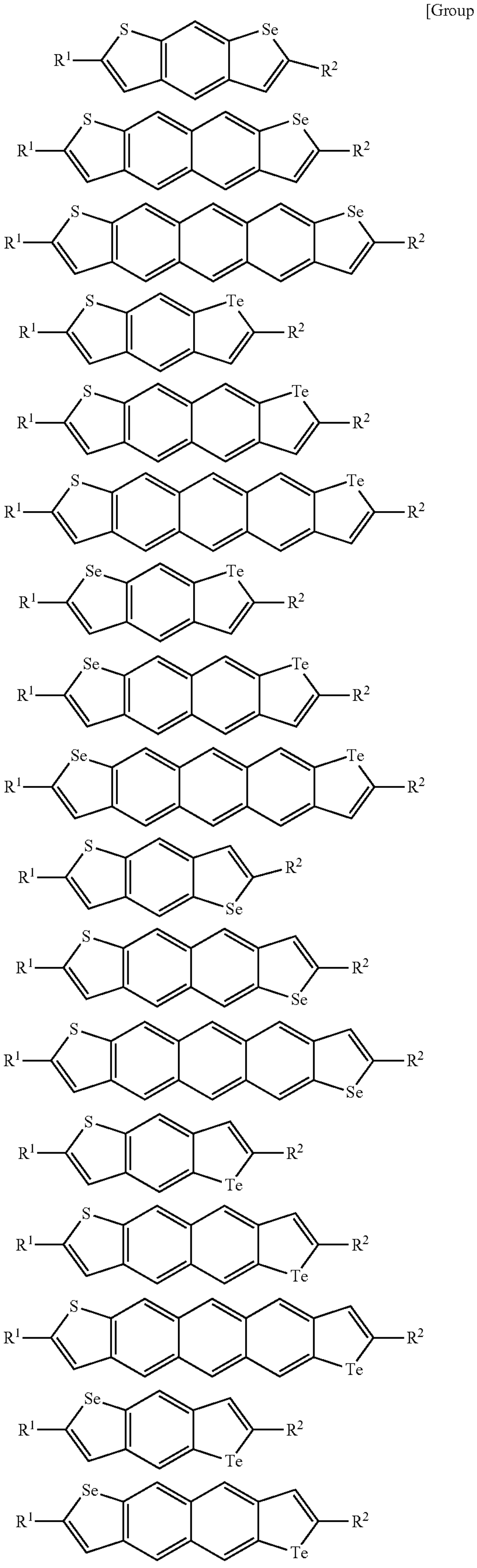

-continued
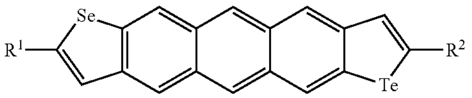
In some embodiments, the compound may include a group listed in Group 2:
[Group 2]
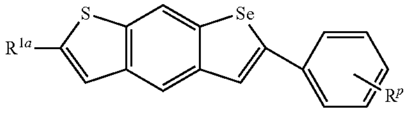
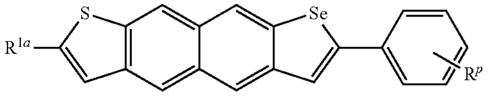
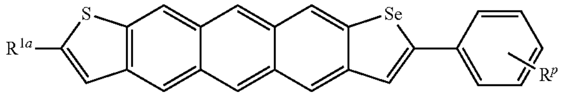
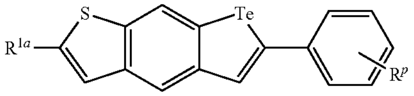
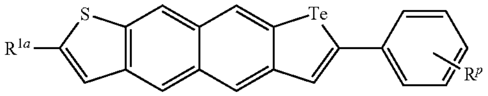
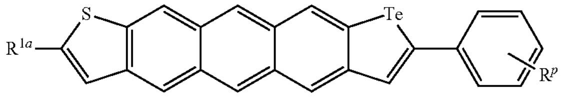
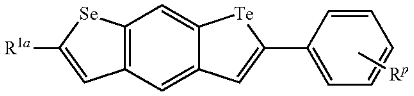
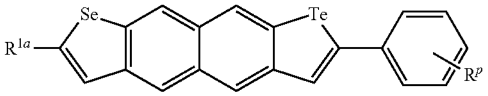
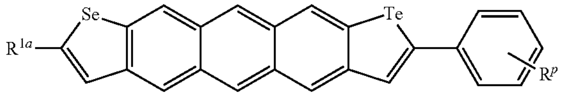
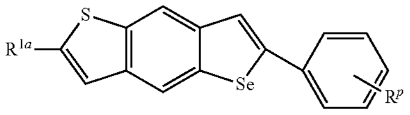
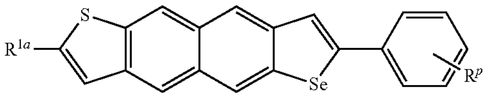
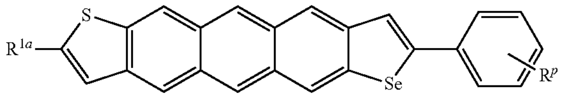
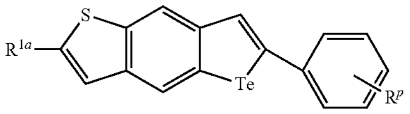
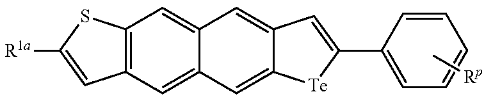
-continued
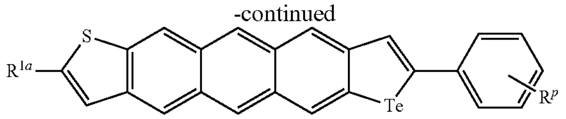
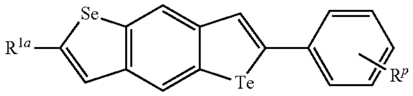
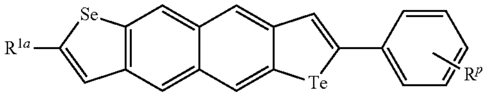
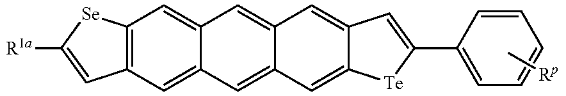
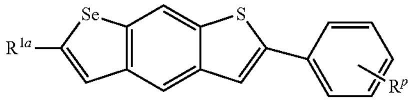
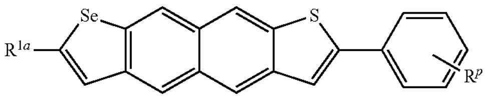
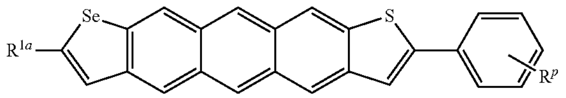
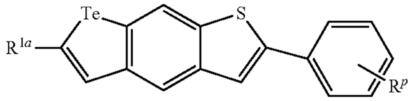
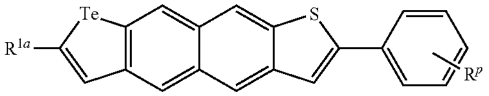
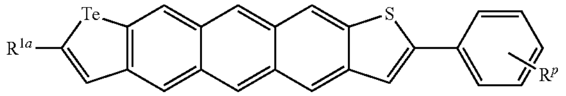
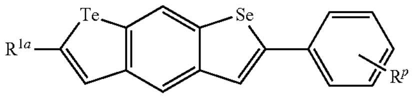
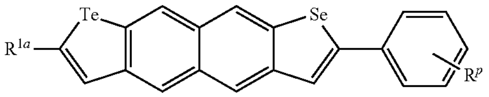
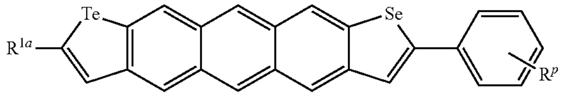
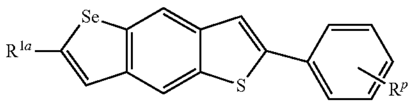
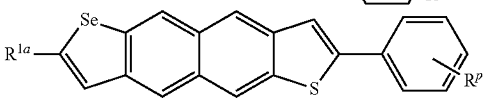
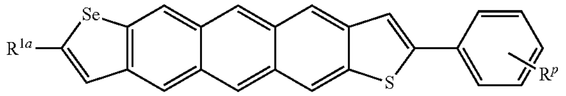
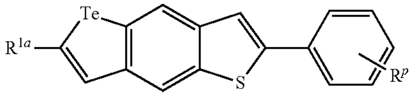
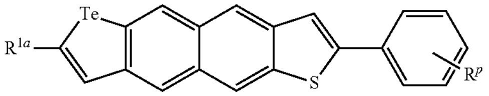

-continued
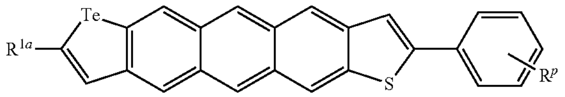
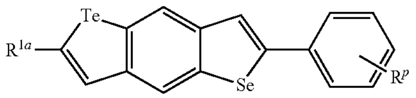
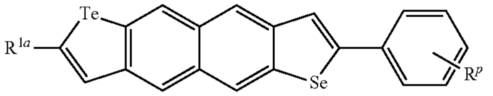
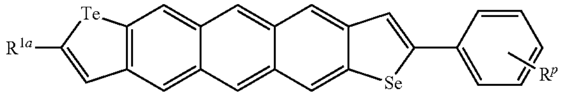
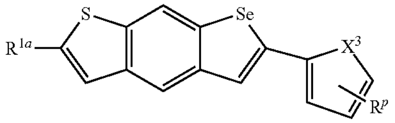
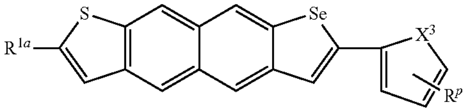
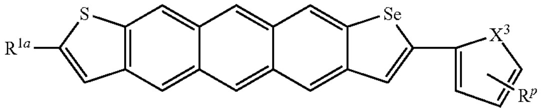
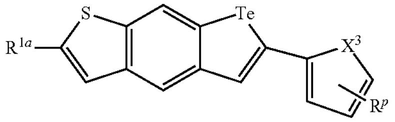
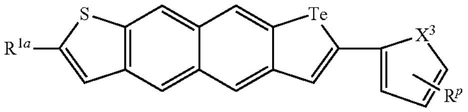
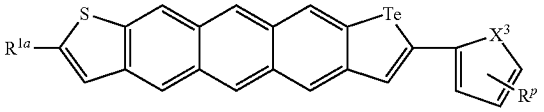
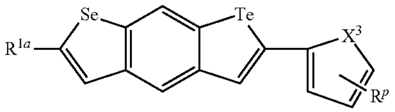
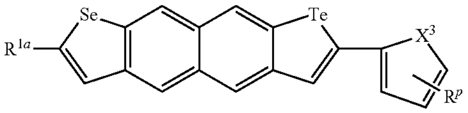
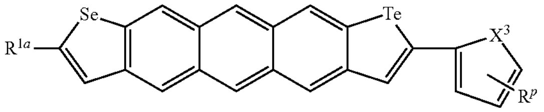
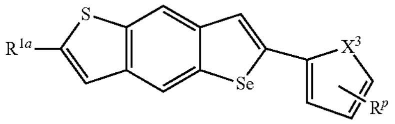
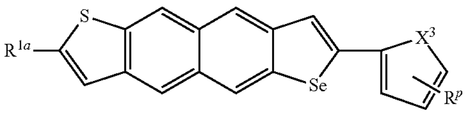
-continued
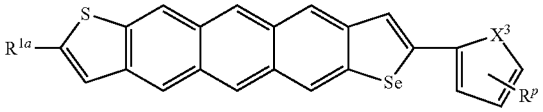
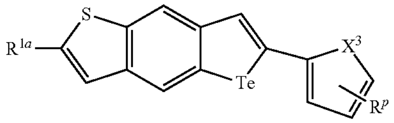
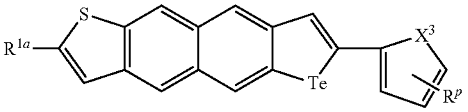
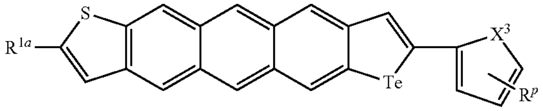
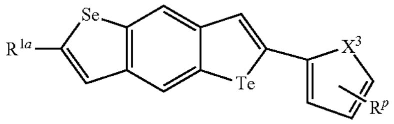
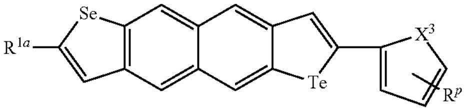
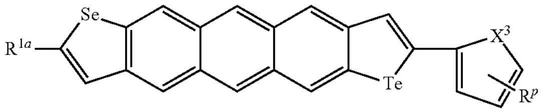
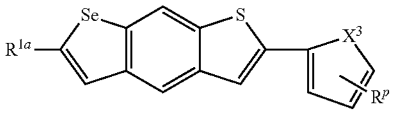
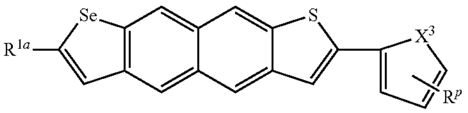
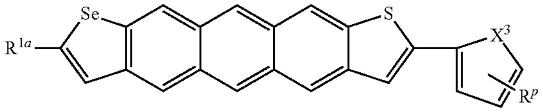
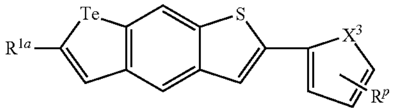
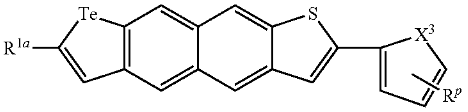
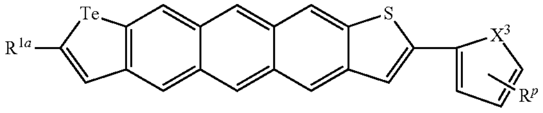
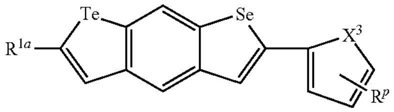
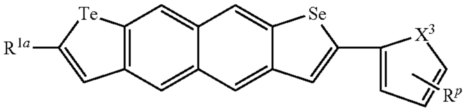

-continued
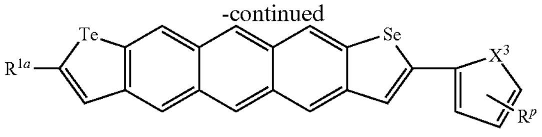
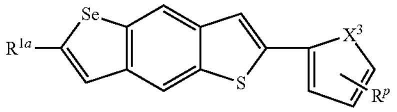
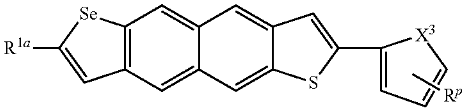
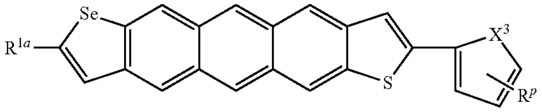
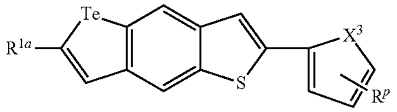
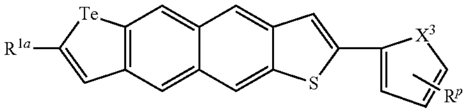
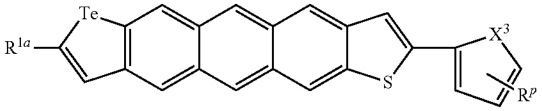
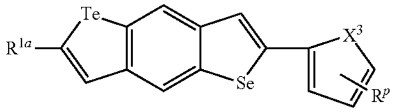
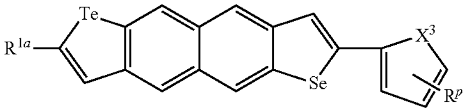
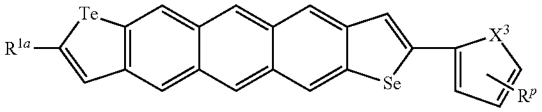
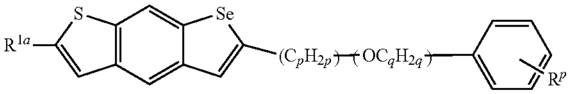
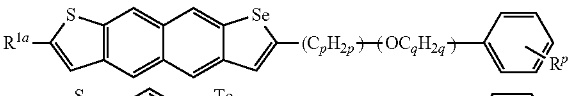
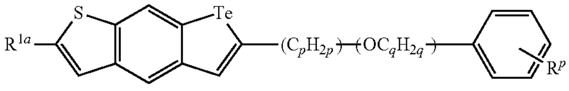
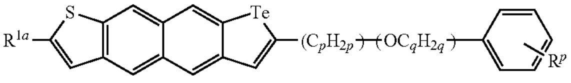
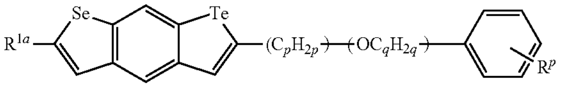
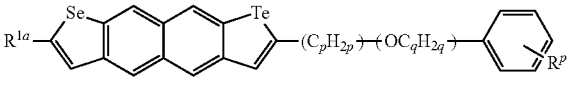
-continued
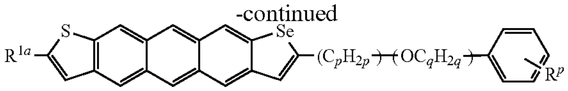
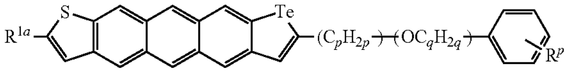
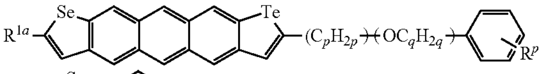
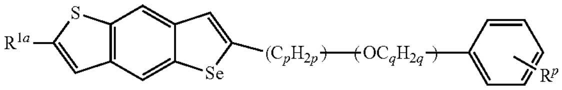
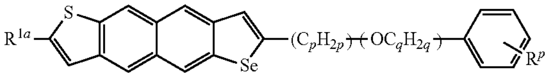
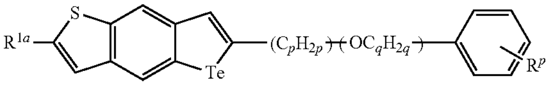
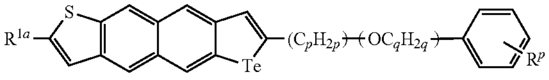
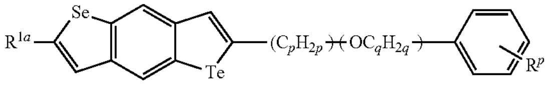
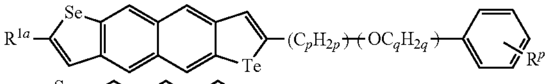
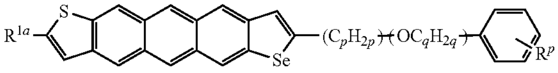
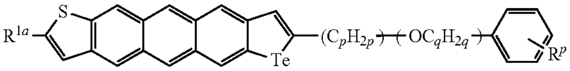
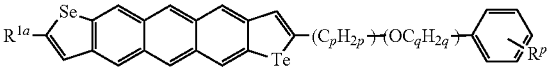
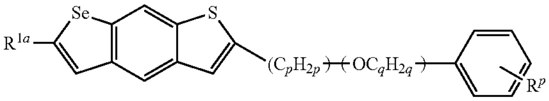
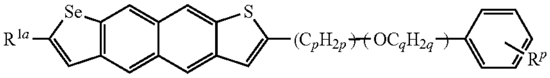
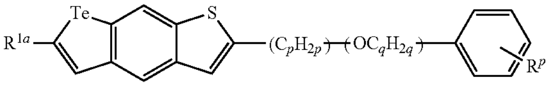
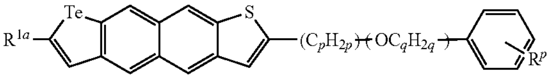
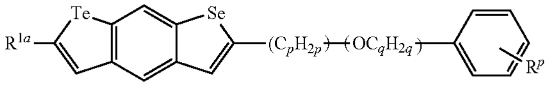
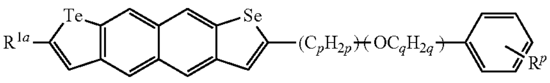
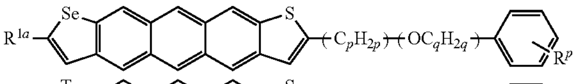
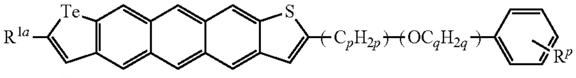
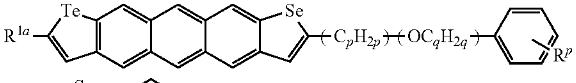
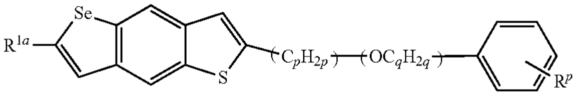

-continued
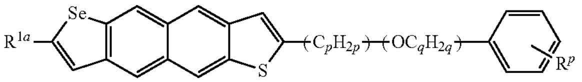
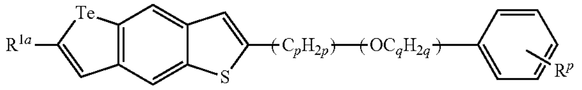
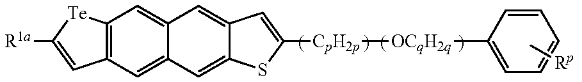
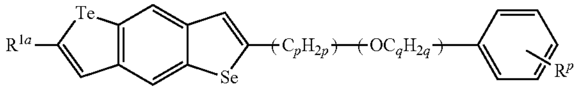
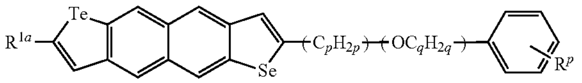
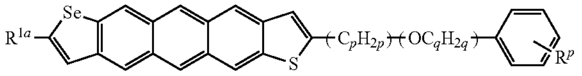
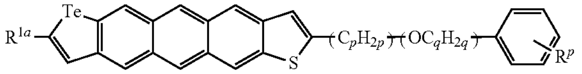
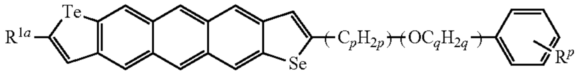
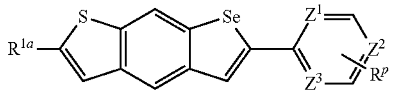
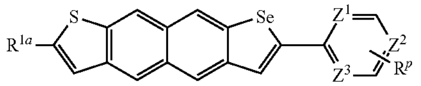
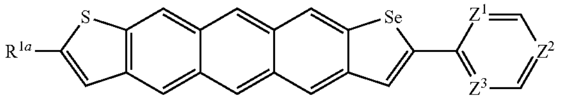
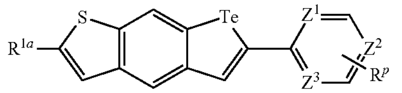
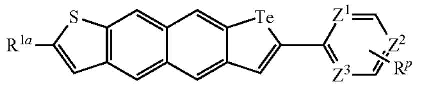
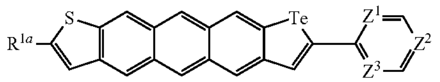
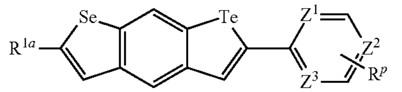
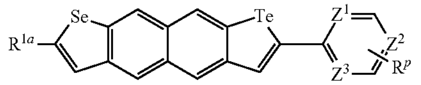
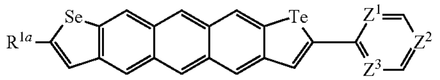
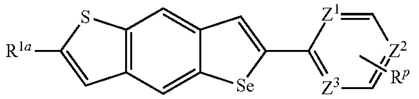
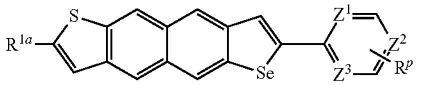
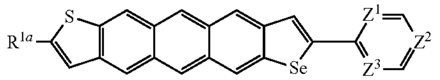
-continued
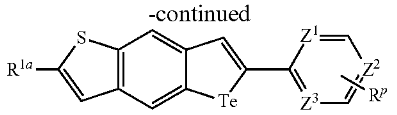
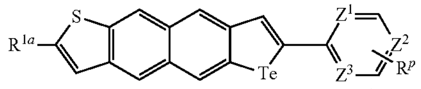
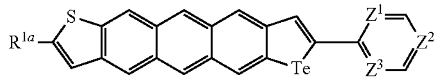
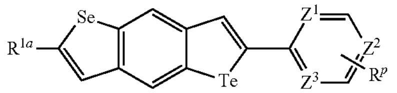
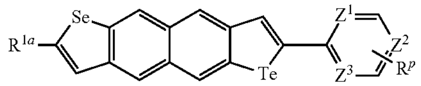
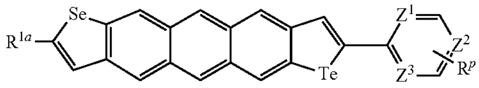
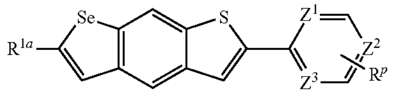
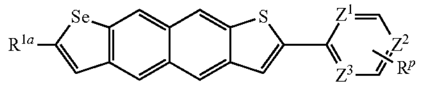
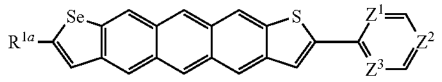
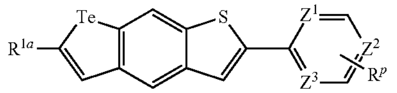
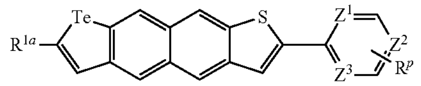
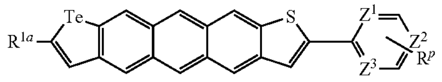
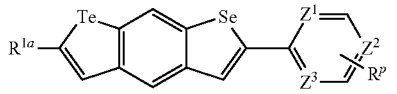
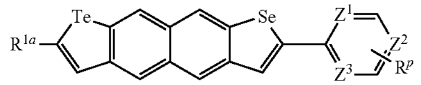
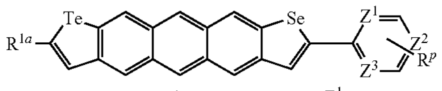
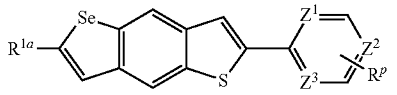
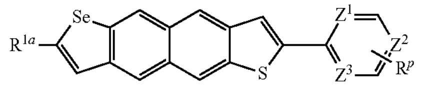
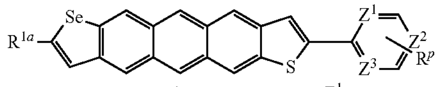
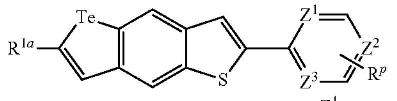
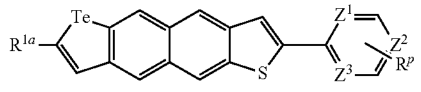

-continued

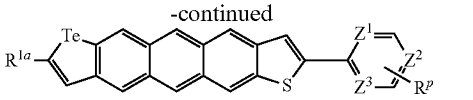

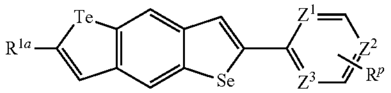

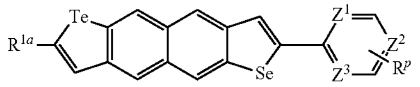

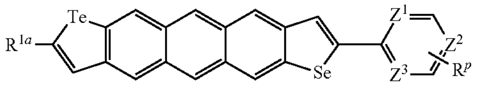

In Group 2, $R^{1a}$ may be hydrogen or a substituted or unsubstituted C1 to C30 alkyl group, $Z^1$ to $Z^3$ may independently be N or $CR^a$, one of $Z^1$ to $Z^3$ may be N, $X^3$ may be one of O, S, Se, Te, $NR^b$, or $CR^cR^d$, p and q independently may be an integer of 1 to 30, and $R^p$ and $R^a$ to $R_d$ may independently be one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

According to another embodiment, an organic thin film including the compound is provided.

According to another embodiment, a thin film transistor may include a gate electrode, an organic semiconductor (also referred to as an organic semiconductor layer) overlapping with the gate electrode, and a source electrode and a drain electrode electrically connected to the organic semiconductor. The organic semiconductor may include a compound represented by Chemical Formula 1A or 1B.

According to yet another embodiment, an electronic device may include the organic thin film.

According to still another embodiment, an electronic device may include the thin film transistor.

The compound may effectively be applied to a deposition or solution process and simultaneously improve charge mobility and current on-off ratio.

DETAILED DESCRIPTION

Figure 1:
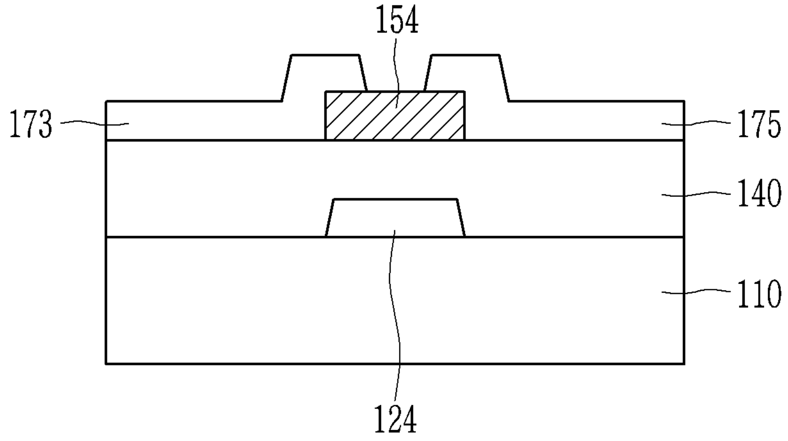
FIG. 1 is a cross-sectional view showing a thin film transistor according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, "substituted" may refer to replacement of hydrogen of a compound or a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" may refer to inclusion of one to four heteroatoms selected from N, O, S, Se, Te, Si, and P.

As used herein, when a definition is not otherwise provided, "alkyl group" may refer to a linear or branched, saturated, monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

As used herein, when a definition is not otherwise provided, "alkenyl group" may refer to a linear or branched, saturated, monovalent hydrocarbon group (e.g., ethenyl group) having at least one carbon-carbon double bond.

As used herein, when a definition is not otherwise provided, "alkynyl group" may refer to a linear or branched saturated monovalent hydrocarbon group including at least one carbon-carbon triple bond (e.g., ethynyl group).

As used herein, when a definition is not otherwise provided, "alkoxy group" may refer to an alkyl group that is linked via oxygen, for example a methoxy, an ethoxy, and a sec-butyloxy group.

As used herein, when a definition is not otherwise provided, "aryl group" may refer to a monovalent functional group formed by the removal of one hydrogen atom from one or more rings of an arene, e.g., phenyl, biphenyl, or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

As used herein, when a definition is not otherwise provided, "heteroaryl group" may refer to an aryl group or a cyclic group including at least one heteroatom selected from N, O, S, Se, Te, P, and Si instead of carbon (C) in the aryl group or the cyclic group. When the heteroaryl group is a fused ring, at least one of rings of the heteroaryl group may have a heteroatom or each ring may have a heteroatom.

As used herein, when a definition is not otherwise provided, "alkylaryl group" may refer to an aryl group where at least one hydrogen atom is replaced by an alkyl group.

As used herein, when a definition is not otherwise provided, "arylalkyl group" may refer to an alkyl group where at least one hydrogen atom is replaced by an aryl group.

As used herein, when a definition is not otherwise provided, "aryloxy group" may refer to an aryl group that is linked via oxygen, and the aryl group is the same as described above.

As used herein, when a definition is not otherwise provided, "arylalkyl group" may refer to an aryl group where at least one hydrogen atom is replaced by a lower alkylene, e.g., methylene, ethylene, propylene, and the like. For example, the "arylalkyl group" may be a benzyl group or a phenylethyl group.

As used herein, when a definition is not otherwise provided, "cycloalkyl group" may refer to a monovalent functional group having one or more saturated rings in which all ring members are carbon, e.g., a cyclopentyl group and a cyclohexyl group.

As used herein, when a definition is not otherwise provided, "heteroalkyl group" may refer to the alkyl group defined above where methylene (—(CH)2-) is replaced by —O—, —S—, —S(═O)2-, —Se—, or —NR— (wherein R is hydrogen or a C1 to C10 alkyl group).

As used herein, when a definition is not otherwise provided, "arylheteroalkyl group" may refer to the heteroalkyl group defined above where at least one hydrogen atom is replaced by an aryl group.

As used herein, when a definition is not otherwise provided, "heteroarylalkyl group" may refer to the alkyl group defined above where at least one hydrogen atom is replaced by a heteroaryl group.

As used herein, when a definition is not otherwise provided, "alkylheteroaryl group" may refer to the heteroaryl group defined above where at least one hydrogen atom is replaced by an alkyl group.

As used herein, when a definition is not otherwise provided, "aromatic ring" may refer to a functional group in which all atoms in the cyclic functional group have a p-orbital, and wherein these p-orbitals are conjugated. For example, the aromatic ring may be a C6 to C20 aryl group.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; C; A and B; A and C; B and C; and A, B, and C."

Hereinafter, a compound according to an embodiment is described.

A compound according to an embodiment may be represented by Chemical Formula 1A or 1B.

[Chemical Formula 1A]

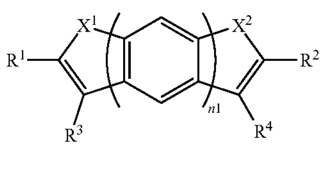

-continued

[Chemical Formula 1B]

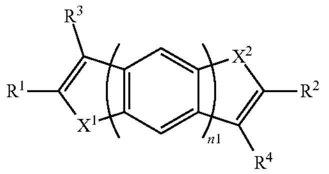

In Chemical Formulae 1A and 1B, $X^1$ and $X^2$ are different from each other and are independently one of O, S, Se, and Te, $R^1$ to $R^4$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is an integer ranging from 1 to 4.

The compound is a fused polycyclic aromatic compound including a fused polycyclic aromatic ring where three to six rings are fused as a core structure. The core structure has a structure where an aryl group located between the pentagonal heterocyclic rings at both terminal ends is fused. The pentagonal heterocyclic rings at both terminal ends have different heteroatoms to form an asymmetric core structure.

Such a fused polycyclic aromatic compound having an asymmetric core structure may have a high crystallinity and thus may improve charge mobility. In addition, the fused polycyclic aromatic compound having an asymmetric core structure may exhibit liquid crystallinity at a desired (and/or alternatively predetermined) temperature region, thereby increasing alignment of molecules. Herein, the temperature region exhibiting liquid crystallinity may be relatively low, thereby lowering a process temperature. Accordingly, the fused polycyclic aromatic compound having an asymmetric core structure may have high charge mobility due to its high crystallinity and molecular arrangement, and simultaneously, the process temperature may be lowered to limit and/or prevent deterioration of the compound and damage caused by cracks of the thin film.

For example, $X^1$ and X2 may be different from each other and may independently be one of S, Se, and Te.

For example, $X^1$ and $X^2$ may be different and one of $X^1$ and $X^2$ may be S.

For example, $X^1$ and $X^2$ may be different and one of $X^1$ and $X^2$ may be Se or Te.

For example, one of $X^1$ and X2 may be S, and the other of $X^1$ and $X^2$ may be Se or Te.

For example, one of $X^1$ and $X^2$ may be Se, and the other of $X^1$ and $X^2$ may be Te.

For example, n1 may be an integer in a range of 1 to 4 and/or 1 to 3, and thus the compound may be a fused polycyclic aromatic compound including a fused polycyclic aromatic ring where three to six rings or three to five rings are fused, as a core structure.

For example, the compound may be an unsubstituted fused polycyclic aromatic compound.

For example, the compound may be a fused polycyclic aromatic compound having at least one substituent, and namely at least one of $R^1$ to $R^4$ may not be hydrogen.

For example, the compound may be a fused polycyclic aromatic compound having an asymmetric substituted structure, and namely $R^1$ and $R^2$ may be different and/or $R^3$ and $R^4$ may be different.

For example, the compound may have a substituent at one side of the fused polycyclic aromatic ring.

For example, one of $R^1$ and $R^2$ may be hydrogen and the other of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

For example, one of $R^3$ and $R^4$ may be hydrogen and the other of $R^3$ and $R^4$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

For example, the compound may have a linear substituent at one side of the fused polycyclic aromatic ring and a non-linear substituent at the other side of the fused polycyclic aromatic ring.

For example, one of $R^1$ and $R^2$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of R1 and $R^2$ may be a substituted or unsubstituted C1 to C30 branched alkyl group, a substituted or unsubstituted C2 to C30 branched alkenyl group, a substituted or unsubstituted C2 to C30 branched alkynyl group, or a combination thereof.

For example, one of $R^3$ and $R^4$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of R3 and R4 may be a substituted or unsubstituted C1 to C30 branched alkyl group, a substituted or unsubstituted C2 to C30 branched alkenyl group, a substituted or unsubstituted C2 to C30 branched alkynyl group, or a combination thereof.

For example, the compound may have a non-cyclic substituent at one side of the fused polycyclic aromatic ring and a cyclic substituent at the other side of the fused polycyclic aromatic ring.

For example, one of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be a substituted or unsubstituted C6 to C30 aryl group, a substituted or unsubstituted C6 to C30 aryloxy group, a substituted or unsubstituted C3 to C30 heteroaryl group, or a combination thereof.

For example, one of $R^3$ and $R^4$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^3$ and $R^4$ may be a substituted or unsubstituted C6 to C30 aryl group, a substituted or unsubstituted C6 to C30 aryloxy group, a substituted or unsubstituted C3 to C30 heteroaryl group, or a combination thereof.

For example, the compound may have a cyclic substituent at one side of the fused polycyclic aromatic ring and a heterocyclic substituent at the other side of the fused polycyclic aromatic ring.

For example, one of $R^1$ and $R^2$ may be one of a substituted or unsubstituted C6 to C30 aryl group or a substituted or unsubstituted C6 to C30 aryloxy group and the other of $R^1$ and $R^2$ may be a substituted or unsubstituted C3 to C30 heteroaryl group.

For example, one of $R^3$ and $R^4$ may be one of a substituted or unsubstituted C6 to C30 aryl group or a substituted or unsubstituted C6 to C30 aryloxy group and the other of $R^3$ and $R^4$ may be a substituted or unsubstituted C3 to C30 heteroaryl group.

For example, one of $R^1$ and $R^2$ may include one of a substituted or unsubstituted C6 to C30 aryl group or a substituted or unsubstituted C3 to C30 heteroaryl group, and for example one of $R^1$ and $R^2$ may include a group represented by one of Chemical Formulae 2A to 2C.

[Compound 2A]

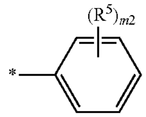

[Compound 2B]

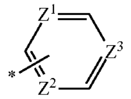

[Compound 2C]

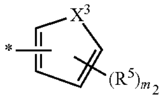

In Chemical Formulae 2A to 2C, $Z^1$ to $Z^3$ are each N or $CR^a$, one of $Z^1$ to $Z^3$ is N, $X^3$ is one of O, S, Se, Te, $NR^b$, or $CR^cR^d$, m1 is an integer ranging from 0 to 5, m2 is an integer ranging from 0 to 3, $R^5$, $R^6$, and $R^a$ to $R^d$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, when m1 is two or more, each $R^5$ is the same or different and two adjacent $R^5$'s are independently present or linked with each other to form a ring, and when m2 is two or more, each $R^6$ is the same or different and two adjacent $R^6$'s are independently present or linked with each other to form a ring.

For example, at least one of $R^3$ and $R^4$ may include one of a substituted or unsubstituted C6 to C30 aryl group or a substituted or unsubstituted C3 to C30 heteroaryl group, and for example one of R3 and R4 may include a group represented by one of Chemical Formulae 2A to 2C.

For example, $R^3$ and $R^4$ may independently be hydrogen.

For example, in Chemical Formula 1A or 1B, $X^1$ may be O or S, $X^2$ may be Se or Te, one of $R^1$ and $R^2$ may be hydrogen, and the other of $R^1$ and $R^2$ may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

For example, in Chemical Formula 1A or 1B, $X^1$ may be O or S, $X^2$ may be Se or Te, one of $R^1$ and $R^2$ may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ may be one of a substituted or unsubstituted C1 to C30 branched alkyl group, a substituted or unsubstituted C2 to C30 branched alkenyl group, a substituted or unsubstituted C2 to C30 branched alkynyl group, or a combination thereof.

For example, in Chemical Formula 1A or 1B, $X^1$ may be O or S, X2 may be Se or Te, one of R1 and R2 may be one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ may be one of a substituted or unsubstituted C1 to C30 branched alkyl group, a substituted or unsubstituted C2 to C30 branched alkenyl group, a substituted or unsubstituted C2 to C30 branched alkynyl group, or a combination thereof.

For example, in Chemical Formula 1A or 1B, X1 may be O or S, X2 may be Se or Te, one of R1 and R2 may be one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of R1 and R2 may be one of a substituted or unsubstituted C6 to C30 aryl group, a substituted or unsubstituted C6 to C30 aryloxy group, a substituted or unsubstituted C3 to C30 heteroaryl group, or a combination thereof.

The compound may be for example one of the compounds of Group 1, but is not limited thereto.

[Group 1]

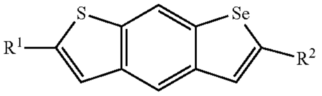

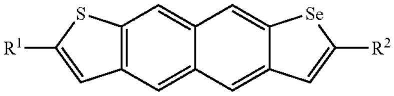

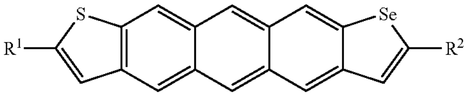

-continued

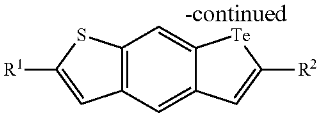

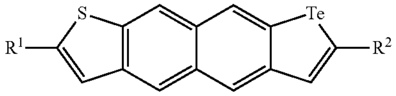

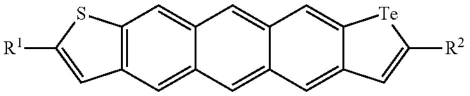

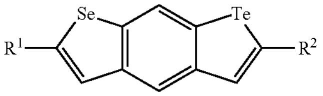

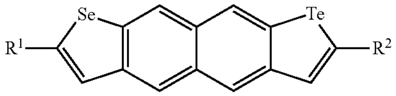

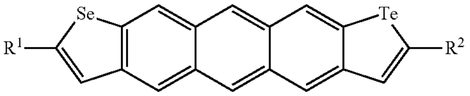

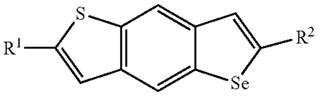

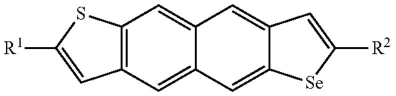

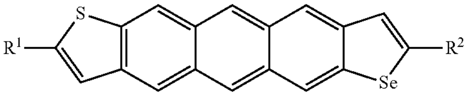

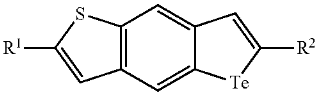

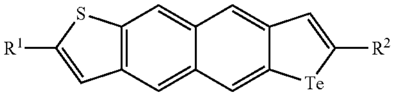

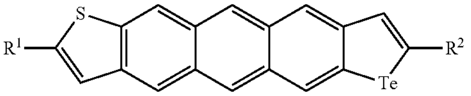

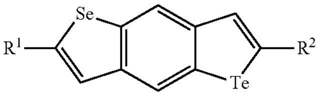

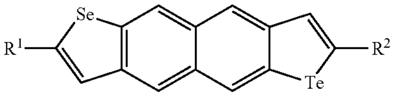

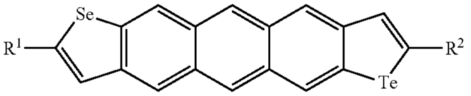

In Group 1, $R^1$ and $R^2$ are the same as described above.

The compound may be for example one of the compounds of Group 2, but is not limited thereto.

[Group 2]

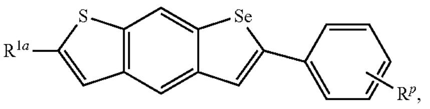

-continued
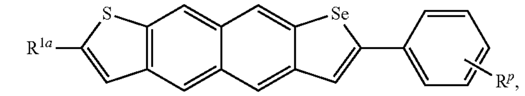,
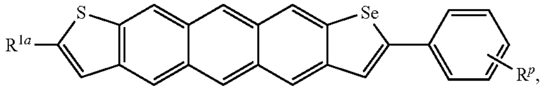,
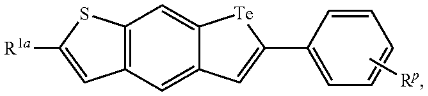,
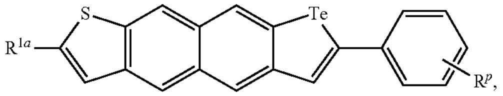,
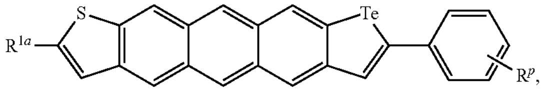,
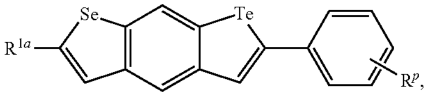,
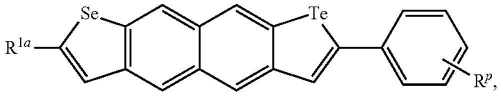,
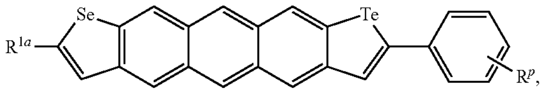,
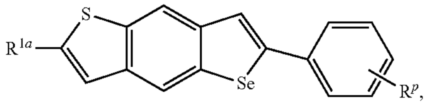,
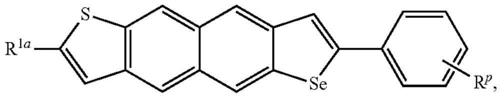,
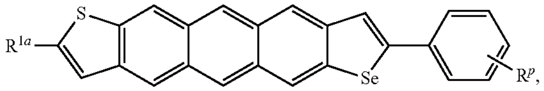,
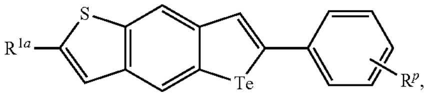,
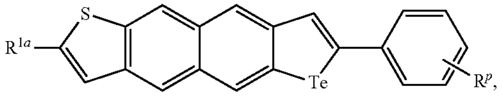,
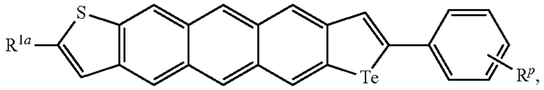,
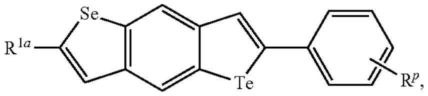,
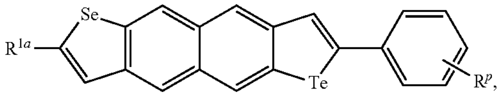,
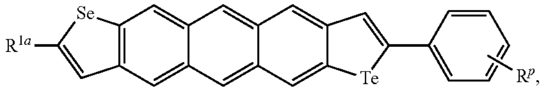,
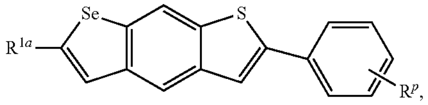,
-continued
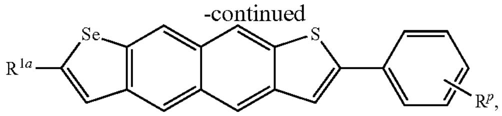,
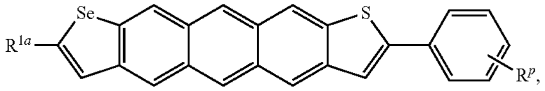,
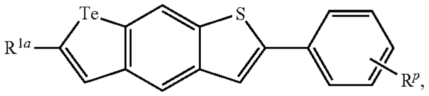,
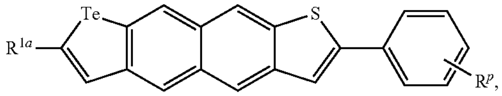,
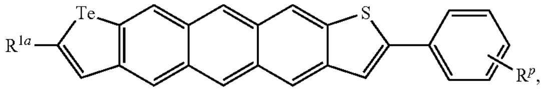,
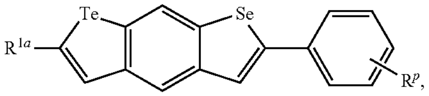,
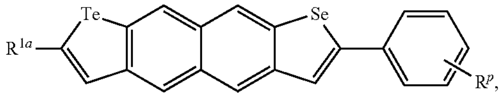,
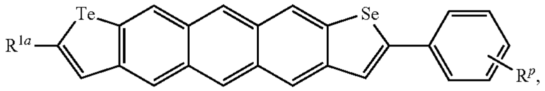,
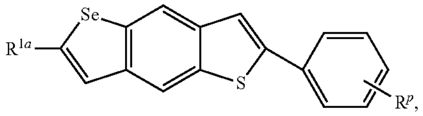,
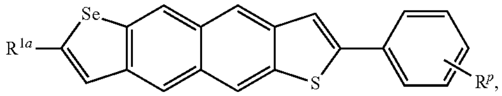,
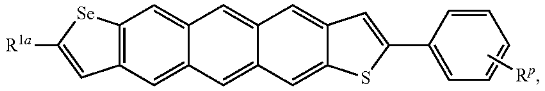,
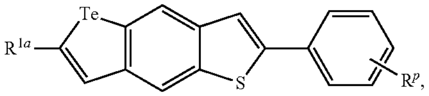,
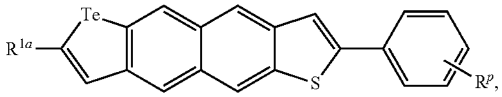,
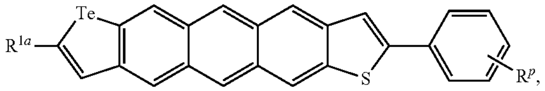,
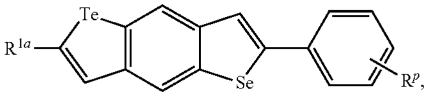,
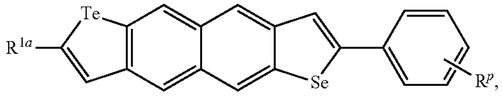,
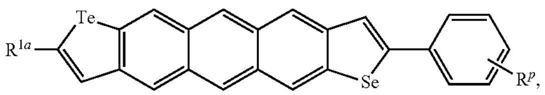,
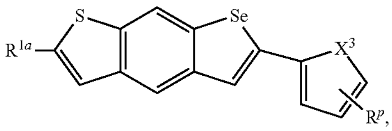, -continued
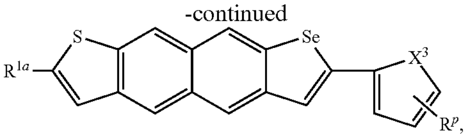
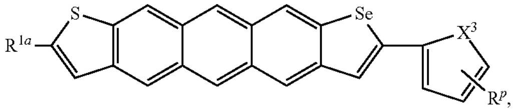
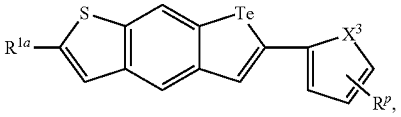
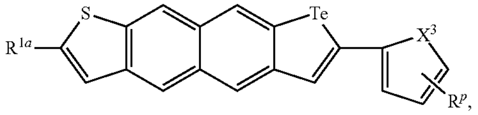
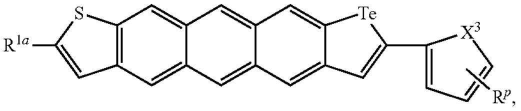
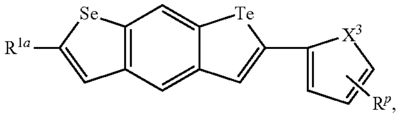
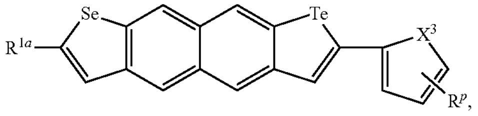
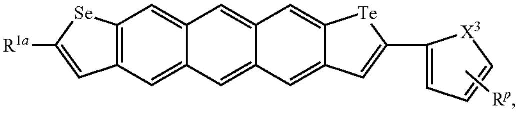
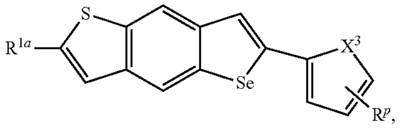
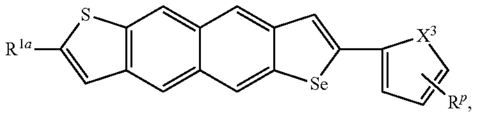
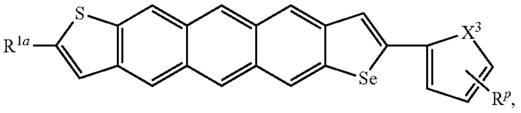
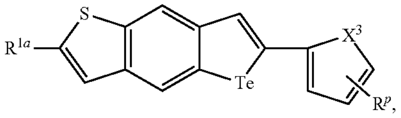
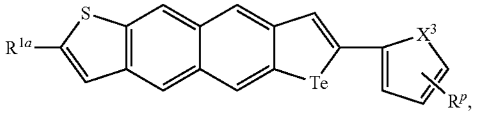
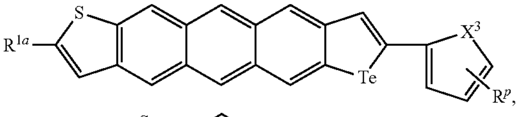
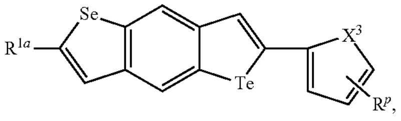
-continued
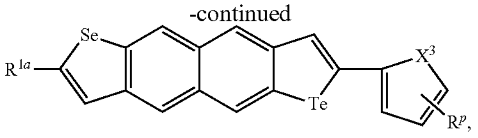
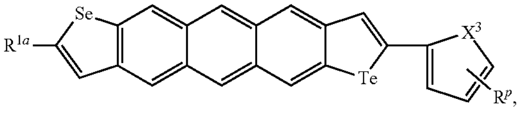
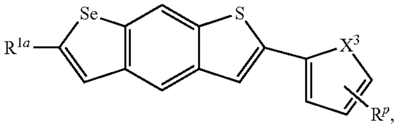
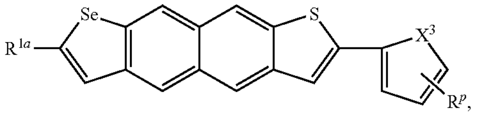
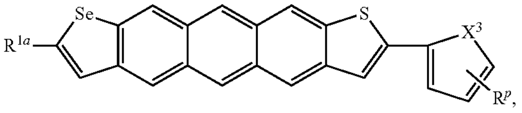
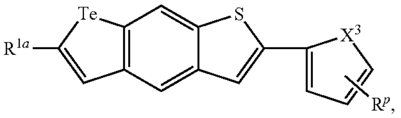
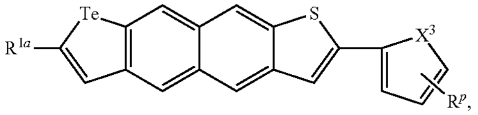
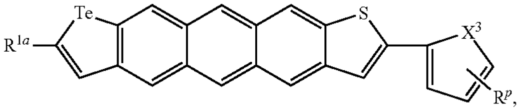
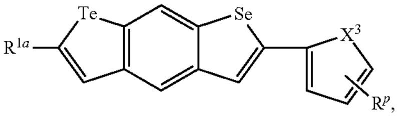
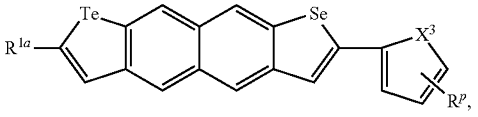
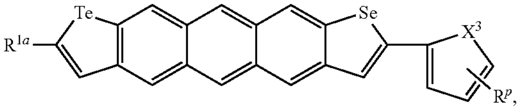
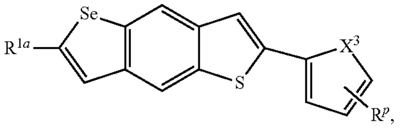
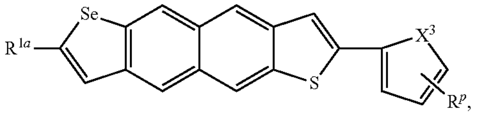
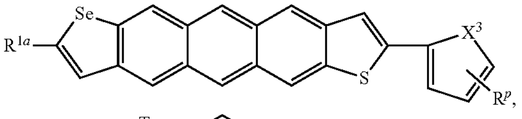
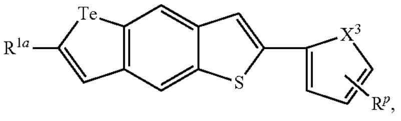

-continued
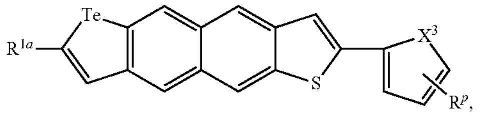
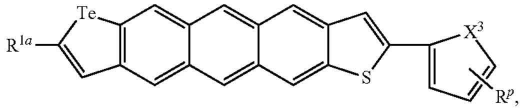
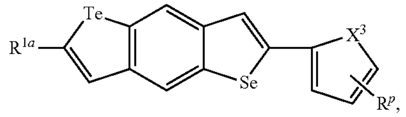
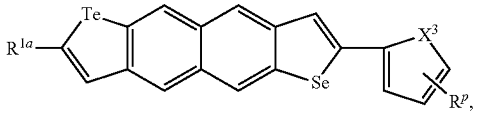
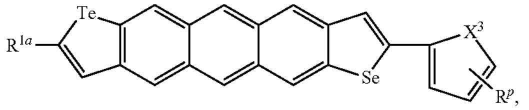
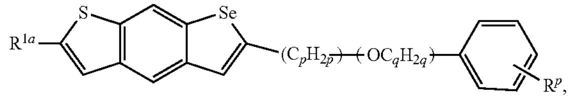
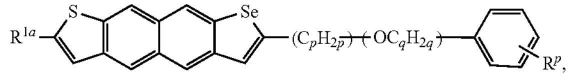
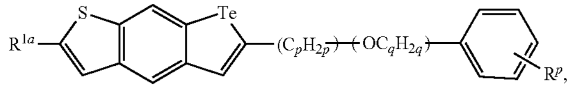
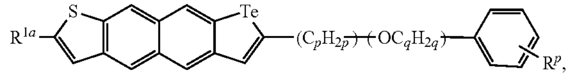
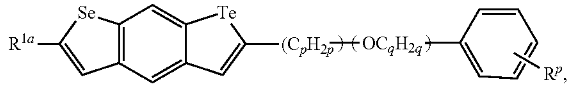
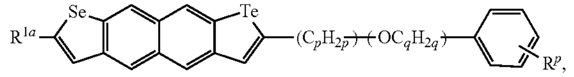
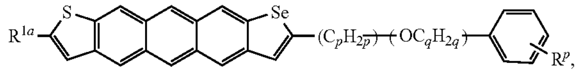
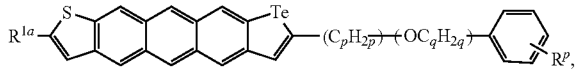
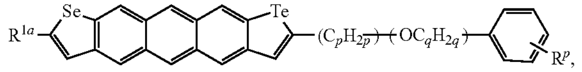
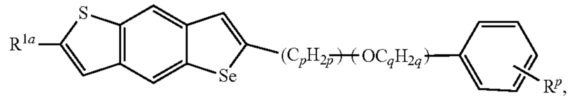
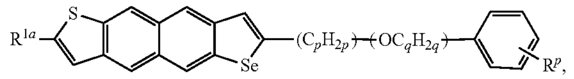
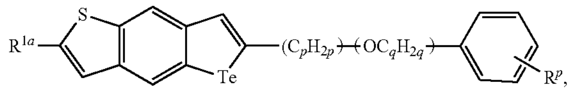
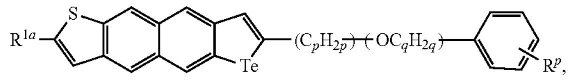
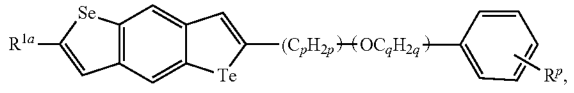
-continued
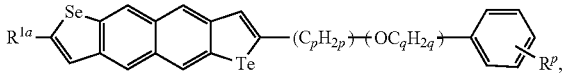
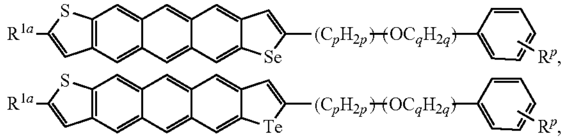
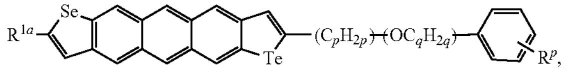
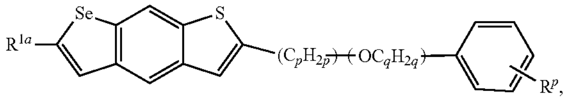
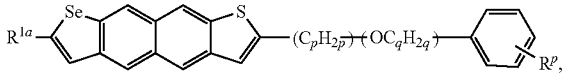
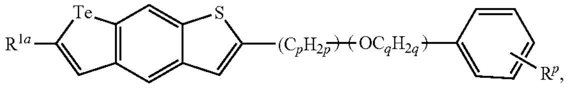
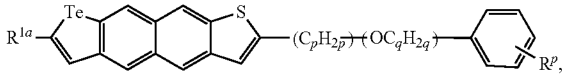
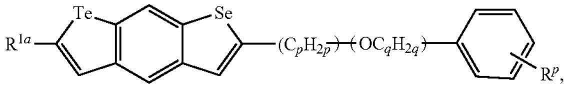
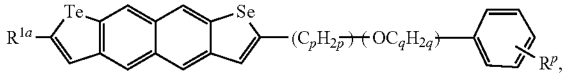
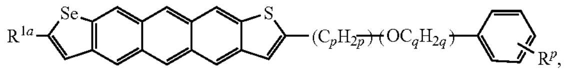
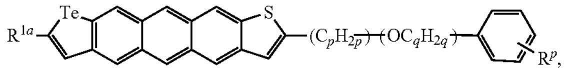
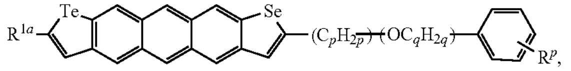
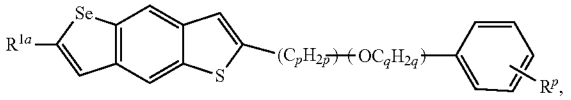
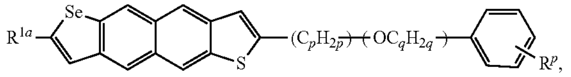
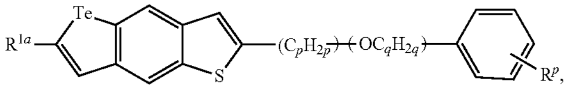
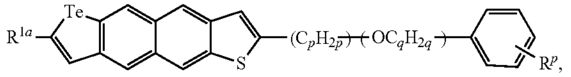
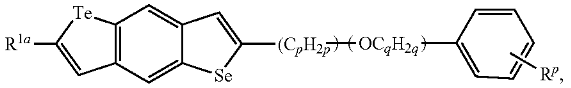
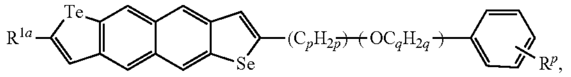
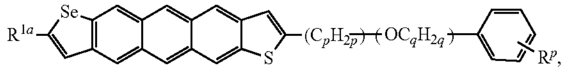
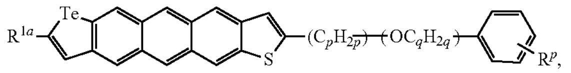
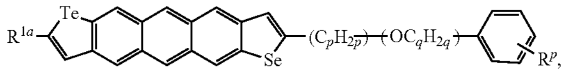

-continued
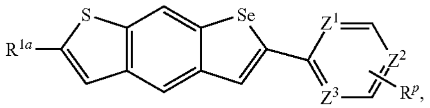
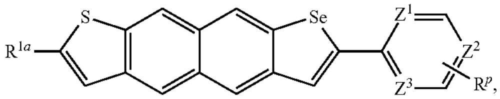
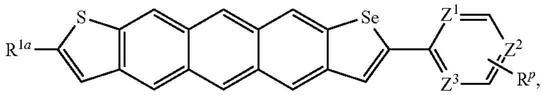
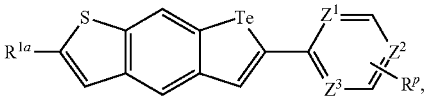
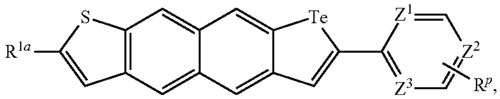
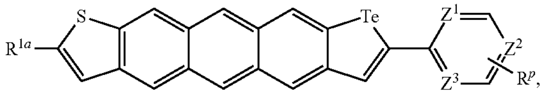
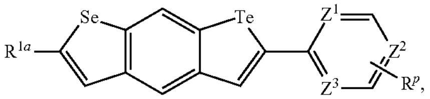
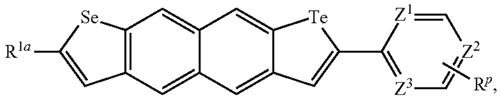
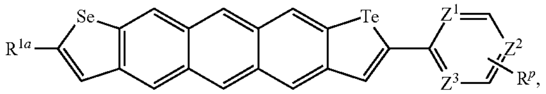
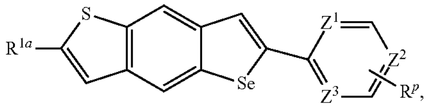
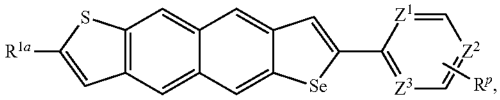
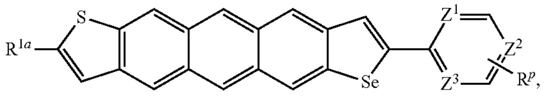
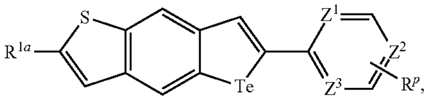
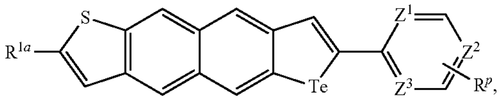
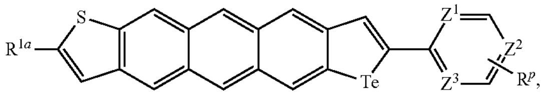
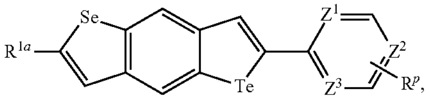
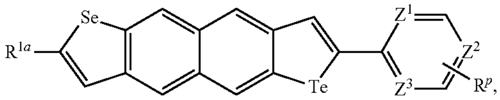
-continued
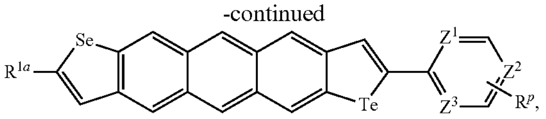
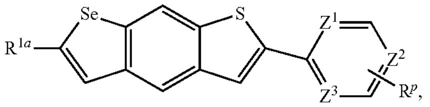
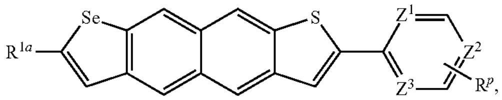
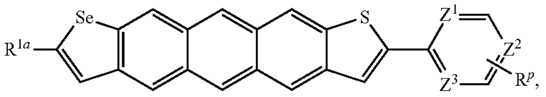
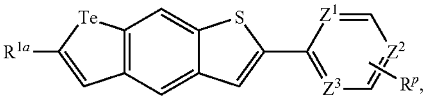
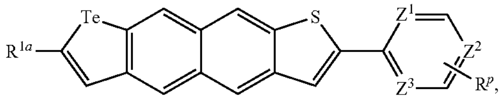
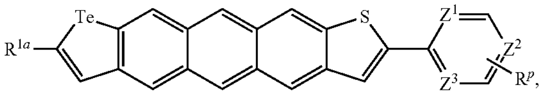
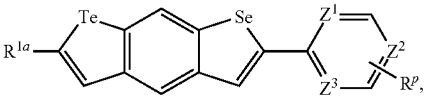
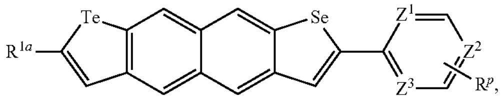
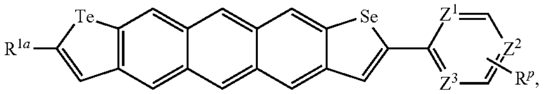
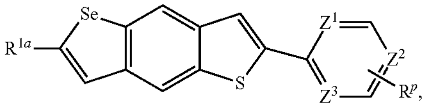
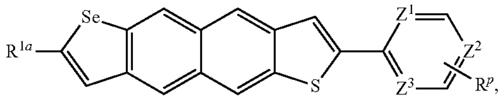
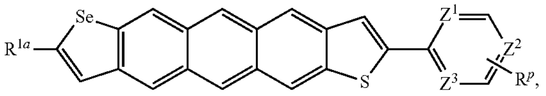
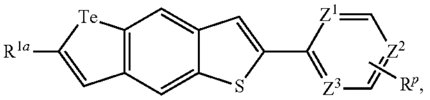
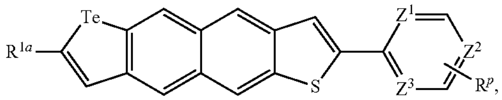
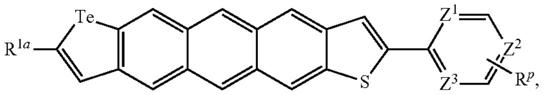
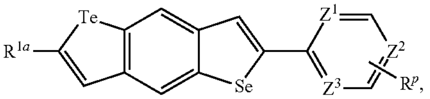

-continued

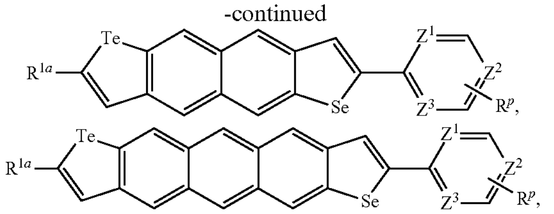

In Group 2, $R^{1a}$ may be hydrogen or a substituted or unsubstituted C1 to C30 alkyl group, $Z^1$ to $Z^3$ may independently be N or $CR^a$, one of $Z^1$ to $Z^3$ may be N, $X^3$ may be one of O, S, Se, Te, $NR^b$, or $CR^cR^d$, p and q may independently be an integer of 1 to 30, and $R^p$ and $R^a$ to $R^d$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

An organic thin film may be formed from the compound. The organic thin film may be formed by a deposition to be a deposited film or the organic thin film may be formed by coating to a coating thin film.

The organic thin film may be applied to various devices including an organic semiconductor. For example, the compound may be applied to a thin film transistor and may be applied to a charge transport layer and/or an active layer of an electronic device such as a solar cell, an organic light emitting diode (OLED) display, and an organic sensor.

Hereinafter, one example of a thin film transistor including the compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view showing a thin film transistor according to an embodiment.

A gate electrode 124 is formed on a substrate 110 made of transparent glass, a semiconductor (e.g., silicon), or plastic. The gate electrode 124 is connected to a gate line (not shown) for transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof. The gate electrode 124 may be formed in the substrate 110 when the substrate 110 is a silicon wafer.

A gate insulating layer 140 is formed on the gate electrode 124. The gate insulating layer 140 may be made of an organic material and/or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride (SiNx) and a silicon oxide ($SiO^2$).

An organic semiconductor 154 is formed on the gate insulating layer 140. The organic semiconductor 154 may include the compound. The organic semiconductor 154 may be formed in a solution process such as spin coating, slit coating, or inkjet printing by preparing the compound in a form of a solution. However, the organic semiconductor 154 may be formed by vacuum-depositing or thermal evaporating the compound. A source electrode 173 and a drain electrode 175 are formed on the organic semiconductor 154. The source electrode 173 and the drain electrode 175 face each other on the organic semiconductor 154. The source electrode 173 is electrically connected to the data line (not shown) transferring the data signal. The source electrode 173 and the drain electrode 175 may include at least one metal of gold (Au), copper (Cu), nickel (Ni), aluminum (Al), molybdenum (Mo), chromium (Cr), tantalum (Ta), titanium (Ti), an alloy thereof, or a combination thereof.

Although the bottom gate structured organic thin film transistor is provided as an example of the organic thin film transistor, the organic thin film transistor is not limited thereto, and all organic thin film transistors including a top gate structured organic thin film transistor may be applied. Although the source electrode 173 and the drain electrode 175 are positioned on the organic semiconductor 154 in FIG. 1, the organic thin film transistor is not limited thereto, and the organic semiconductor 154 may be positioned on the source electrode 173 and the drain electrode 175.

The thin film transistor may be applied to a switch or driving device of various electronic devices, and the electronic device may include, for example, a liquid crystal display (LCD), an organic light emitting diode (OLED) display, an electrophoretic display, an organic photoelectric device, and an organic sensor, but is not limited thereto.

Hereinafter, the embodiments are illustrated in more detail with reference to examples. However, these examples are non-limiting, and inventive concepts are not thereto.

Synthesis of Compound

Synthesis Example 1

[Reaction Scheme 1]

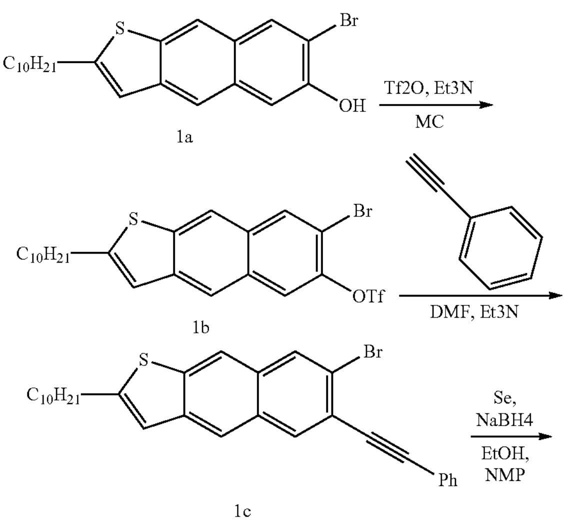

-continued

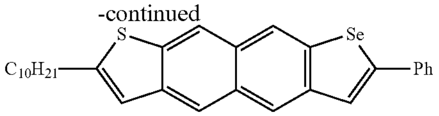

1d

Synthesis of Compound 1b

Compound 1a (1 g, 2.38 mmol) (herein, $C_{10}H_{21}$ group is a linear alkyl group) is dissolved in 50 mL of dry methyl dichloride (MC), and the resultant solution is cooled down to 0° C. Subsequently, triethylamine ($Et_3N$, 0.9 mL, 6.43 mmol) is added thereto, and the obtained mixture is stirred for 1 hour at 0° C. Then, trifluoromethanesulfonic anhydride ($Tf_2O$, 0.6 mL, 3.58 mmol) is slowly added thereto in a dropwise fashion, and the obtained mixture is slowly heated up to room temperature and stirred for 12 hours. Subsequently, 30 mL of an ammonium chloride-saturated aqueous solution is added thereto, and an extract is obtained therefrom by using methyl dichloride and then, several times washed with water. Subsequently, the extract is dried with magnesium sulfate, filtered, and after removing a solvent therefrom, purified through silica column chromatography to obtain Compound 1b. A yield is 96%.

1H NMR (300 MHz, CDCl3): δ ppm 8.19 (s, 2H), 8.12 (s, 1H), 7.89 (s, 1H), 7.09 (s, 1H), 2.94 (t, 2H), 1.79 (m, 2H), 1.36 (m, 14H), 0.87 (t, 3H)

Synthesis of Compound 1c

Compound 1b (1.26 g, 2.28 mmol), bis(triphenylphosphine) palladium (II) dichloride ($Pd(PPh_3)_2Cl_2$, 0.08 g, 0.11 mmol), and CuI (0.04 g, 0.23 mmol) are dissolved in dimethyl formamide (30 mL) and triethylamine (6 mL), and the resultant solution is cooled down to −78° C. Subsequently, ethynylbenzene (0.38 mL, 3.42 mmol) is added thereto, and the obtained mixture is stirred for 5 hours, while slowly heated up to room temperature. Then, 30 mL of an ammonium chloride-saturated aqueous solution is added thereto, and an extract is obtained therefrom by using chloroform and then, several times washed with water. The extract is dried with magnesium sulfate, filtered, and after removing solvent therefrom, purified through silica column chromatography to obtain Compound 1c. A yield is 82%.

1H NMR (300 MHz, CDCl3): δ ppm 8.18 (s, 1H), 8.14 (d, 2H), 8.06 (s, 1H), 7.63 (m, 2H), 7.39 (m, 3H), 7.07 (s, 1H), 2.92 (t, 2H), 1.78 (m, 2H), 1.36 (m, 14H), 0.88 (t, 3H)

Synthesis of Compound 1d

Se (1.22 g, 15.5 mmol) is dissolved in 100 mL of ethanol, the resultant solution is cooled down to 0° C., and $NaBH_4$ (0.59 g, 15.5 mmol) is added thereto. The resulting material is dissolved in 15 mL of N-methyl-2-pyrrolidone, and Compound 1c (5.2 g, 10.32 mmol) is added thereto. After increasing the temperature up to 130° C., the obtained mixture is stirred for 12 hours and cooled down to room temperature, and a solid produced therein is washed with methanol and chloroform to obtain Compound 1d as a yellow solid. A yield is 58%.

MS (MALDI-TOF-MS, m/z) 504.315

Comparative Synthesis Example 1

[Reaction Scheme 2]

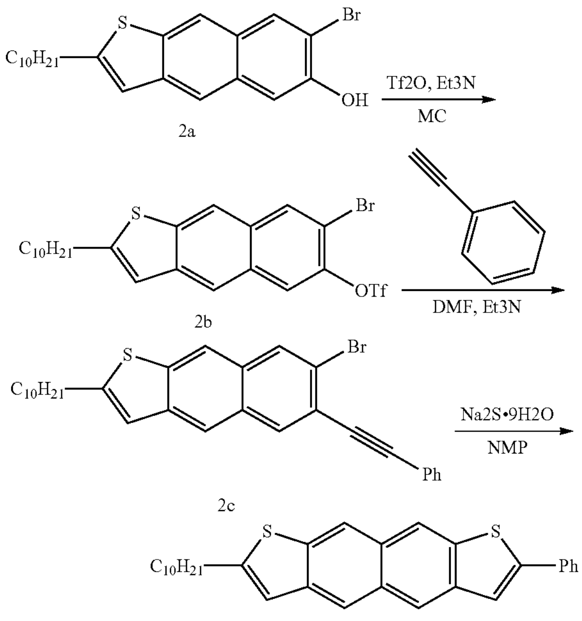

2d

Synthesis of Compound 2b

Compound 2a (1 g, 2.38 mmol) is dissolved in 50 mL of dry methyl dichloride, and the resultant solution is cooled down to 0° C. Subsequently, triethylamine ($Et_3N$, 0.9 mL, 6.43 mmol) is added thereto, and the obtained mixture is stirred for 1 hour at 0° C. Then, trifluoromethanesulfonic anhydride ($Tf_2O$, 0.6 mL, 3.58 mmol) is slowly added thereto in a dropwise fashion, and the obtained mixture is heated up to room temperature and stirred for 12 hours. Subsequently, 30 mL of an ammonium chloride-saturated aqueous solution is added thereto, and an extract is obtained therefrom by using methyl dichloride and then, several times washed with water. The extract is dried with magnesium sulfate, filtered, and after removing a solvent therefrom, purified through silica column chromatography to obtain Compound 2b. A yield is 96%.

1H NMR (300 MHz, CDCl3): δ ppm 8.19 (s, 2H), 8.12 (s, 1H), 7.89 (s, 1H), 7.09 (s, 1H), 2.94 (t, 2H), 1.79 (m, 2H), 1.36 (m, 14H), 0.87 (t, 3H)

Synthesis of Compound 2c

Compound 2b (1.26 g, 2.28 mmol), bis(triphenylphosphine) palladium (II) dichloride (0.08 g, 0.11 mmol), and CuI (0.04 g, 0.23 mmol) are dissolved in 30 mL of dimethyl formamide and 6 mL of triethylamine, and the resultant solution is cooled down to −78° C. Subsequently, ethynylbenzene (0.38 mL, 3.42 mmol) is added thereto, and the obtained mixture is stirred for 5 hours, while heated up to room temperature. Then, 30 mL of an ammonium chloride-saturated aqueous solution is added thereto, and an extract is obtained therefrom by using chloroform and then, several times washed with water. The extract is dried by using magnesium sulfate, filtered, and after removing a solvent therefrom, purified through silica column chromatography to obtain Compound 2c. A yield is 82%.

1H NMR (300 MHz, CDCl3): δ ppm 8.18 (s, 1H), 8.14 (d, 2H), 8.06 (s, 1H), 7.63 (m, 2H), 7.39 (m, 3H), 7.07 (s, 1H), 2.92 (t, 2H), 1.78 (m, 2H), 1.36 (m, 14H), 0.88 (t, 3H)

Synthesis of Compound 2d

Compound 2c (0.55 g, 1.09 mmol) is dissolved in 50 mL of N-methyl-2-pyrrolidone, and $Na_2S_9H_2O$ (0.63 g, 2.62 mmol) is added thereto. After increasing the temperature up to 110° C., the obtained mixture is stirred for 2 hours. Subsequently, after decreasing the temperature down to room temperature, a yellow solid produced therefrom is washed with chloroform and methanol and collected to obtain Compound 2d. A yield is 80%.

MS (MALDI-TOF-MS, m/z) 456.343 (M+)

Synthesis Example 2

[Reaction Scheme 3]

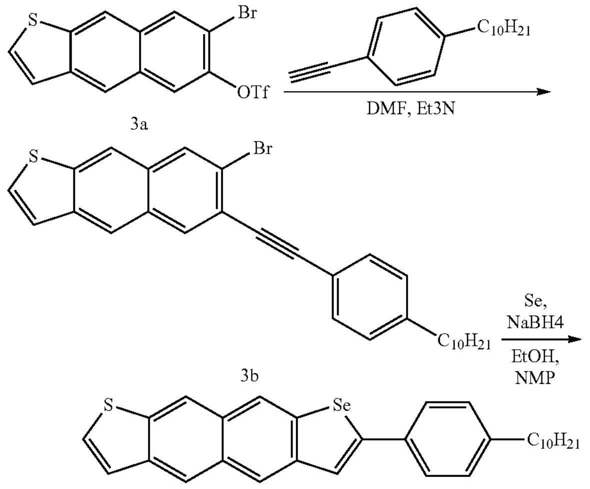

3c

Synthesis of Compound 3b

Compound 3a (5 g, 12.2 mmol), bis(triphenylphosphine) palladium (II) dichloride (0.43 g, 0.6 mmol), and CuI (0.23 g, 1.2 mmol) are dissolved in 125 mL of dimethyl formamide and 25 mL of triethylamine, and the resultant solution is cooled down to −78° C. Subsequently, ethynylbenzene (3.2 g, 13.2 mmol) is added thereto, and the obtained mixture is stirred for 5 hours, while slowly heated up to room temperature. Then, 200 mL of distilled water is added thereto, and an extract is obtained therefrom with chloroform and then, several times washed with water. The extract is dried with magnesium sulfate, filtered, dried again, and a volume of chloroform is reduced, and after adding hexane ten times as much as the chloroform thereto, a solid produced therein is filtered to obtain Compound 3b as a white solid. A yield is 65%.

1H NMR (300 MHz, CDCl3): δ ppm 8.25 (s, 2H), 8.20 (d, 2H), 7.56 (s, 1H), 7.55 (d, 2H), 7.43 (d, 1H), 7.20 (d, 2H), 2.63 (t, 2H), 1.62 (m, 2H), 1.30 (m, 14H), 0.88 (t, 3H)

Synthesis of Compound 3c

Se (1.2 g, 15.5 mmol) is dissolved in 100 mL of ethanol, the resultant solution is cooled down to 0° C., and $NaBH_4$ (0.98 g, 25.8 mmol) is added thereto. Subsequently, Compound 3b (4.7 g, 9.3 mmol) dissolved in 500 mL of N-methyl-2-pyrrolidone is added thereto. The obtained mixture is heated up to 130° C., stirred for 12 hours, and cooled down to room temperature, and a solid produced therein is washed with methanol and chloroform to obtain Compound 3c as a yellow solid. A yield is 66%.

MS (MALDI-TOF-MS, m/z) 504.220

Comparative Synthesis Example 2

[Reaction Scheme 4]

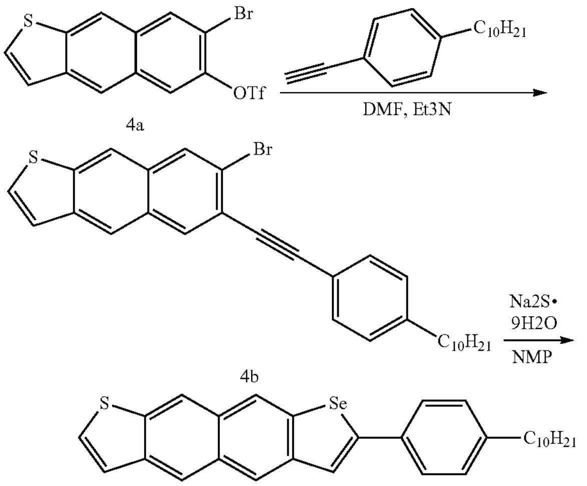

4c

Synthesis of Compound 4b

Compound 4a (5 g, 12.2 mmol), bis(triphenylphosphine) palladium (II) dichloride (0.43 g, 0.6 mmol), and CuI (0.23 g, 1.2 mmol) are dissolved in 125 mL of dimethyl formamide and 25 mL of triethylamine, and the solution is cooled down to −78° C. Subsequently, ethynylbenzene (3.2 g, 13.2 mmol) is added thereto, and the obtained mixture is stirred for 5 hours, while slowly heated up to room temperature. Then, 200 mL of distilled water is added thereto, and an extract is obtained therefrom by using chloroform and then, several times washed with water. The extract is dried with magnesium sulfate, filtered, dried again, and a volume of chloroform is reduced, and after adding hexane ten times as much as the chloroform, a solid produced therein is filtered to obtain Compound 4b as a white solid. A yield is 65%.

1H NMR (300 MHz, CDCl3): δ ppm 8.25 (s, 2H), 8.20 (d, 2H), 7.56 (s, 1H), 7.55 (d, 2H), 7.43 (d, 1H), 7.20 (d, 2H), 2.63 (t, 2H), 1.62 (m, 2H), 1.30 (m, 14H), 0.88 (t, 3H)

Synthesis of Compound 4c

Compound 4b (3.3 g, 6.55 mmol) is dissolved in N-methyl-2-pyrrolidone, and $Na_2S_9H_2O$ (4.7 g, 19.66 mmol) is added thereto. Subsequently, the obtained mixture is heated up to 110° C. and then, stirred for 2 hours. After decreasing the temperature down to room temperature, a yellow solid produced therein is washed with chloroform and methanol and collected to obtain Compound 4c. A yield is 80%.

MS (MALDI-TOF-MS, m/z) 456.325 (M+)

Formation of Thin Film

Preparation Example 1

The compound according to Synthesis Example 1 is vacuum vapor-deposited on a silicon wafer covered with 3000 Å thick $SiO_2$ at 70° C. to form a 600 Å-thick organic thin film.

Preparation Example 2

An organic thin film is formed according to the same method as Preparation Example 1 except for using the compound according to Synthesis Example 2 instead of the compound according to Synthesis Example 1.

Comparative Preparation Example 1

An organic thin film is formed according to the same method as Preparation Example 1 except for using the compound according to Comparative Synthesis Example 1 instead of the compound according to Synthesis Example 1.

Comparative Preparation Example 2

An organic thin film is formed according to the same method as Preparation Example 1 except for using the compound according to Comparative Synthesis Example 2 instead of the compound according to Synthesis Example 1.

Evaluation I

Crystallinity of the organic thin films according to Preparation Examples 1 and 2 and Comparative Preparation Examples 1 and 2 is examined.

The crystallinity is evaluated by comparing a full width at half maximum (FWHM) from an XRD spectrum peak measured with D8 Advance made by Bruker Company.

Figure 2:
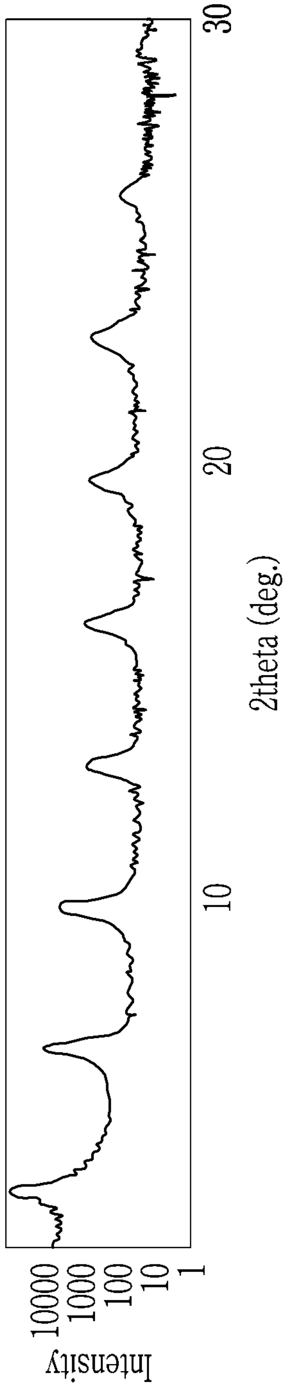
FIG. 2 is a graph showing XRD of the organic thin film according to Preparation Example 1.
Figure 3:
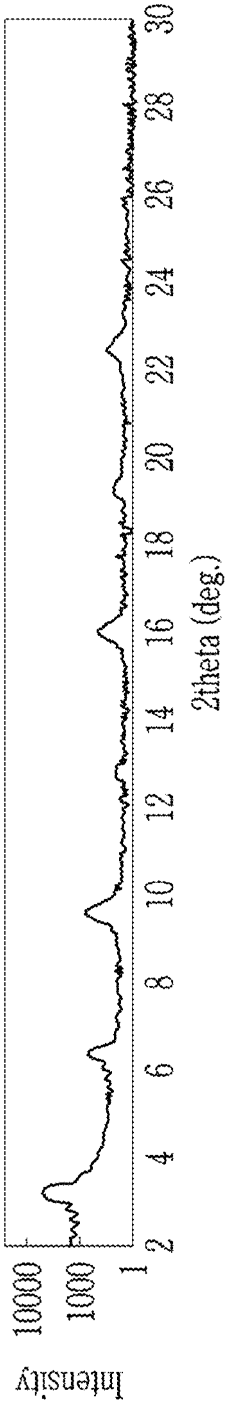
FIG. 3 is a graph showing XRD of the organic thin film according to Comparative Preparation Example 1.
Figure 4:
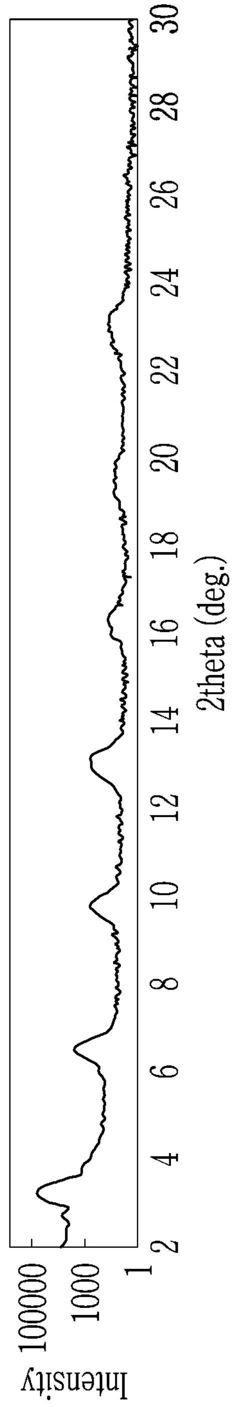
FIG. 4 is a graph showing XRD of the organic thin film according to Preparation Example 2.
Figure 5:
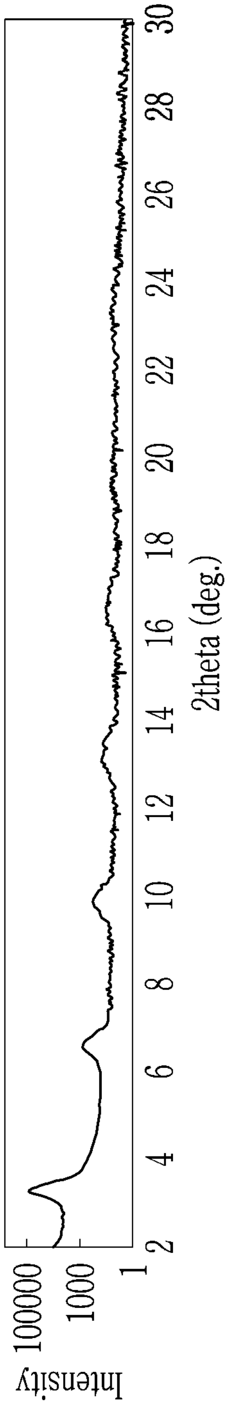
FIG. 5 is a graph showing XRD of the organic thin film according to Comparative Preparation Example 2.

FIG. 2 is a graph showing XRD of the organic thin film according to Preparation Example 1, FIG. 3 is a graph showing XRD of the organic thin film according to Comparative Preparation Example 1, FIG. 4 is a graph showing XRD of the organic thin film according to Preparation Example 2, and FIG. 5 is a graph showing XRD of the organic thin film according to Comparative Preparation Example 2.

Referring to FIGS. 2 and 3, the organic thin film according to Preparation Example 1 shows higher crystallinity than that of organic thin film according to Comparative Preparation Example 1. Likewise, referring to FIGS. 4 and 5, the organic thin film according to Preparation Example 2 shows higher crystallinity than that of organic thin film according to Comparative Preparation Example 2. Accordingly, the fused polycyclic aromatic compound having an asymmetric core structure may show higher crystallinity than the fused polycyclic aromatic compound having a symmetric core structure.

Evaluation II

Thermal properties of the organic thin films according to Preparation Examples 1 and 2 are examined.

The thermal properties of the organic thin films are evaluated through TA Instruments Discovery Differential Scanning calorimeter (Discovery DSC).

The results are shown in Table 1.

TABLE 1

| | Liquid Crystal Phase Transition Temperature (° C.) |
|---|---|
| Preparation Example 1 | 140 |
| Preparation Example 2 | 140 |

Referring to Table 1, the thin films according to Preparation Examples 1 and 2 are present as a liquid crystal at a desired (and/or alternatively predetermined) temperature region, and accordingly, a molecular alignment in the liquid crystal phase section may be expected to be improved through a heat treatment.

Manufacture of Thin Film Transistor

Example 1-1

First, a silicon wafer substrate coated with 3000 Å thick $SiO_2$ is exposed to 02 plasma and then, dipped in an octadecyl trichlorosilane solution diluted in hexane to a concentration of 4 mM to change the surface to be hydrophobic. Subsequently, the compound obtained in Synthesis Example 1 is vacuum-vapor deposited on the substrate to be 500 Å thick at a substrate temperature of 70° C. to form an organic semiconductor. Then, source and drain electrodes are formed on the organic semiconductor by using a shadow mask and depositing Au to be 1000 Å thick to manufacture a thin film transistor.

Example 1-2

A thin film transistor is manufactured according to the same method as Example 1-1, except for additionally annealing the organic semiconductor on a hot plate in a nitrogen glove box at 100° C. for 10 hours in the step of forming the organic semiconductor.

Example 1-3

First, a silicon wafer substrate coated with 3000 Å thick $SiO_2$ is exposed to 02 plasma, dipped in a trimethoxy (2-phenylethyl)silane ((3-PTS) solution diluted to be a concentration of 4 mM in toluene for one hour, and then has an extra solution on the surface removed, and exposed to ammonia vapor for greater than or equal to 10 hours to modify the surface with β-PTS. Subsequently, the compound according to Synthesis Example 1 is dissolved to be a concentration of 0.4 wt % in an o-dichlorobenzene solvent, and a solution obtained therefrom is dripped on the substrate on a hot plate heated at 120° C. to form an organic semiconductor in a gap cast method (for example, refer to Adv.Mater.2011, 23, p. 3681 to 3685). Then, source and drain electrodes are formed on the organic semiconductor by using a shadow mask and depositing Au to be 1000 Å thick to manufacture a thin film transistor.

Example 1-4

A thin film transistor is manufactured according to the same method as Example 1-3, except for additionally annealing the organic semiconductor on a hot plate in a nitrogen glove box at 100° C. for 10 hours in the step of forming the organic semiconductor.

Example 2-1

A thin film transistor is manufactured according to the same method as Example 1-1, except for using the compound according to Synthesis Example 2 instead of the compound according to Synthesis Example 1.

Example 2-2

A thin film transistor is manufactured according to the same method as Example 2-1, except for additionally annealing the organic semiconductor on a hot plate in a nitrogen glove box at 140° C. for 2 hours in the step of forming the organic semiconductor.

Example 2-3

A thin film transistor is manufactured according to the same method as Example 1-3 except for using the compound according to Synthesis Example 2 instead of the compound according to Synthesis Example 1 and a 0.2 wt % concentration solution instead of the 0.4 wt % concentration solution.

Comparative Example 1-1

A thin film transistor is manufactured according to the same method as Example 1-3 except for using the compound according to Comparative Synthesis Example 1 instead of the compound according to Synthesis Example 1.

Comparative Example 1-2

A thin film transistor is manufactured according to the same method as Example 1-3, except for using the compound according to Comparative Synthesis Example 1 instead of the compound according to Synthesis Example 1 and a 0.2 wt % concentration solution instead of the 0.4 wt % concentration solution.

Comparative Example 2-1

A thin film transistor is manufactured according to the same method as Example 1-1, except for using the compound according to Comparative Synthesis Example 2 instead of the compound according to Synthesis Example 1.

Comparative Example 2-2

A thin film transistor is manufactured according to the same method as Example 1-3, except for using the compound according to Comparative Synthesis Example 2 instead of the compound according to Synthesis Example 1 and a 0.2 wt % concentration solution instead of the 0.4 wt % concentration solution.

Evaluation III

Charge mobility of the thin film transistors according to Examples and Comparative Examples is calculated.

The charge mobility of the thin film transistors is calculated by obtaining a graph having $(I_{SD})^{1/2}$ and $V_G$ as variables from a saturation region current equation and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{PBT} = (\text{slope})^2\frac{2L}{C_0 W}$$

In the equations, $I_{SD}$ is a source-drain current, μ or $\mu_{FET}$ is charge mobility, $C_0$ is electrostatic capacitance of a gate insulating layer, W is a channel width, L is a channel length, $V_G$ is a gate voltage, and $V_T$ is a threshold voltage.

A cut-off leakage current ($I_{off}$) is obtained as a minimum current in an off-state as a current flowing in an off-state. A current on-off ratio ($I_{on}/I_{off}$) is obtained as a ratio of a maximum current in an on-state relative to a minimum current in the off-state.

The results are shown in Tables 2 to 5.

TABLE 2

| | Charge mobility ($cm^2/Vs$) | Current on-off ratio ($I_{on}/I_{off}$) |
|---|---|---|
| Example 1-1 | $1.3 \times 10^{-1}$ | $9.8 \times 10^5$ |
| Example 1-2 | $3.7 \times 10^{-1}$ | $3.1 \times 10^6$ |
| Comparative Example 1-1 | $9.5 \times 10^{-3}$ | $3.0 \times 10^5$ |

TABLE 3

| | Charge mobility ($cm^2/Vs$) | Current on-off ratio ($I_{on}/I_{off}$) |
|---|---|---|
| Example 1-3 | $2.1 \times 10^{-1}$ | $1.7 \times 10^4$ |
| Example 1-4 | $3.3 \times 10^{-1}$ | $2.4 \times 10^5$ |
| Comparative Example 1-2 | $4.0 \times 10^{-3}$ | $1.0 \times 10^3$ |

TABLE 4

| | Charge mobility ($cm^2/Vs$) | Current on-off ratio ($I_{on}/I_{off}$) |
|---|---|---|
| Example 2-1 | $1.6 \times 10^{-1}$ | $2.7 \times 10^5$ |
| Example 2-2 | $3.3 \times 10^{-1}$ | $5.6 \times 10^6$ |
| Comparative Example 2-1 | $9.3 \times 10^{-3}$ | $3.3 \times 10^3$ |

TABLE 5

| | Charge mobility ($cm^2/Vs$) | Current on-off ratio ($I_{on}/I_{off}$) |
|---|---|---|
| Example 2-3 | $1.4 \times 10^{-1}$ | $2.5 \times 10^4$ |
| Comparative Example 2-2 | $3.7 \times 10^{-3}$ | $3.8 \times 10^2$ |

Referring to Tables 2 to 5, the thin film transistors according to Examples show improved charge mobility and current on-off ratios compared with the thin film transistors according to Comparative Examples. In addition, the thin film transistors according to Examples 1-2, 1-4, and 2-2 show much improved charge mobility and current on-off ratios through the additional annealing. Furthermore, the thin film transistors according to Examples 1-3, 1-4, and 2-3 have equivalent electrical characteristics in a solution process to in a deposition process. Accordingly, a fused polycyclic aromatic compound having an asymmetric core structure shows improved electrical characteristics.

While some example embodiments have been described, one of ordinary skill in the art would understand that inventive concepts are not limited to the disclosed embodiments, but, on the contrary, may include various modifications and equivalent arrangements included within the spirit and scope of the appended claims.

What is claimed is:

1. A thin film transistor comprising a gate electrode, an organic semiconductor overlapping with the gate electrode, and a source electrode and a drain electrode electrically connected to the organic semiconductor, the organic semiconductor including a compound represented by Chemical Formula 1A or 1B,

[Chemical Formula 1A]

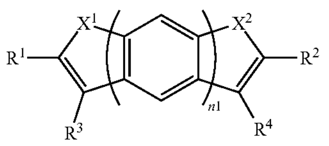

[Chemical Formula 1B]

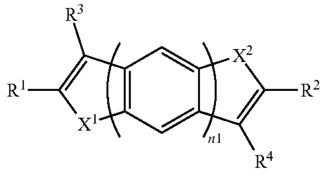

wherein, in Chemical Formulae 1A and 1B, $X^1$ and $X^2$ are different from each other and are independently one of O, S, Se, and Te, provided that one of $X^1$ and $X^2$ is Se or Te, $R^1$ to $R^4$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, provided that $R^1$ and $R^2$ are different from each other, and $n_1$ is an integer ranging from 2 to 4, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

2. The thin film transistor of claim 1, wherein the other of $X^1$ and $X^2$ is S.

3. The thin film transistor of claim 1, wherein one of $R^1$ and $R^2$ is hydrogen, the other of $R^1$ and $R^2$ is one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

4. The thin film transistor of claim 1, wherein one of $R^1$ and $R^2$ is one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, the other of $R^1$ and $R^2$ is one of a substituted or unsubstituted C1 to C30 branched alkyl group, a substituted or unsubstituted C2 to C30 branched alkenyl group, a substituted or unsubstituted C2 to C30 branched alkynyl group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

5. The thin film transistor of claim 1, wherein one of $R^1$ and $R^2$ is one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of $R^1$ and $R^2$ is one of a substituted or unsubstituted C6 to C30 aryl group, a substituted or unsubstituted C6 to C30 aryloxy group, a substituted or unsubstituted C3 to C30 heteroaryl group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

6. The thin film transistor of claim 1, wherein one of $R^1$ and $R^2$ is a group represented by one of Chemical Formulae 2A to 2C:

[Compound 2A]

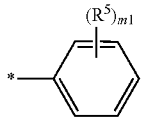

[Compound 2B]

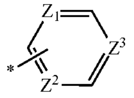

[Compound 2C]

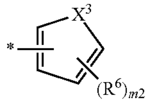

wherein, in Chemical Formulae 2A to 2C, $Z^1$ to $Z^3$ are independently N or $CR^a$, one of $Z^1$ to $Z^3$ is N, $X^3$ is one of O, S, Se, Te, $NR^b$, or $CR^cR^d$, $m_1$ is an integer ranging from 0 to 5, $m_2$ is an integer ranging from 0 to 3, $R^5$, $R^6$ and $R^a$ to $R^d$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, when $m_1$ is two or more, each $R^5$ is the same or different and two adjacent $R^5$'s are independently present or linked with each other to form a ring, and when $m_2$ is two or more, each $R^6$ is the same or different and two adjacent $R^6$'s are independently present or linked with each other to form a ring, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

7. The thin film transistor of claim 1, wherein $X^1$ is O or S, $X^2$ is Se or Te, one of $R^1$ and $R^2$ is hydrogen, and the other of $R^1$ and $R^2$ is one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

8. The thin film transistor of claim 1, wherein $X^1$ is O or S, $X^2$ is Se or Te, one of $R^1$ and $R^2$ is one of a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ is one of a substituted or unsubstituted C1 to C30 branched alkyl group, a substituted or unsubstituted C2 to C30 branched alkenyl group, a substituted or unsubstituted C2 to C30 branched alkynyl group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

9. The thin film transistor of claim 1, wherein $X^1$ is O or S, $X^2$ is Se or Te, one of $R^1$ and $R^2$ is one of a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of $R^1$ and $R^2$ is one of a substituted or unsubstituted C6 to C30 aryl group, a substituted or unsubstituted C6 to C30 aryloxy group, a substituted or unsubstituted C3 to C30 heteroaryl group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

10. The thin film transistor of claim 1, wherein the compound is represented by a structure among structures in Group 1:

[Group 1]

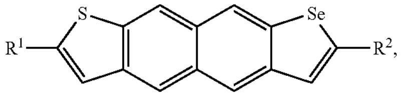

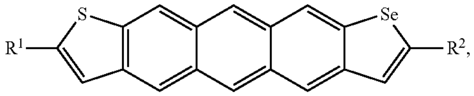

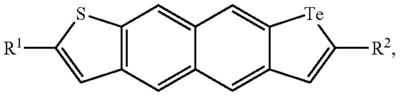

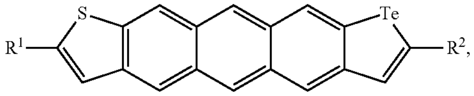

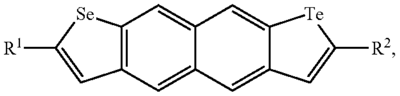

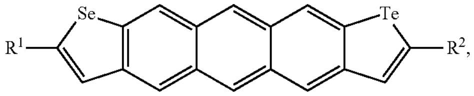

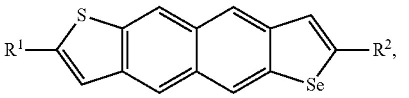

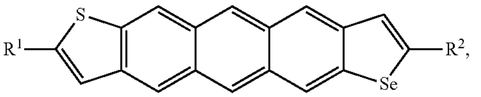

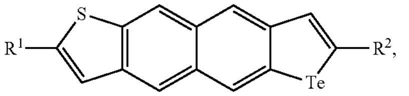

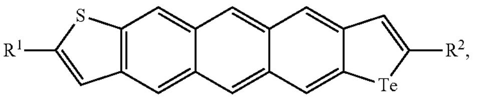

-continued

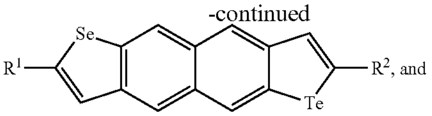

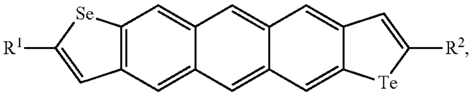

wherein, in Group 1, $R^1$ and $R^2$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, provided that $R^1$ and $R^2$ are different from each other, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

11. The thin film transistor of claim 1, wherein the compound is represented by a structure among structures in Group 2:

[Group 2]

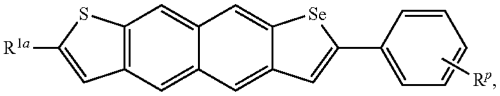

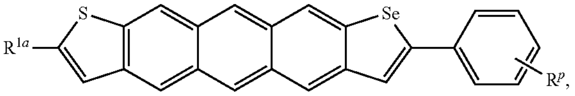

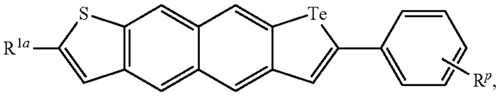

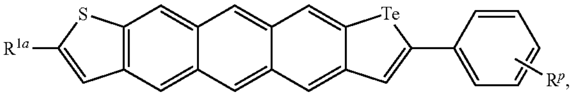

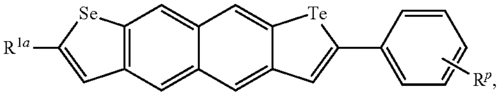

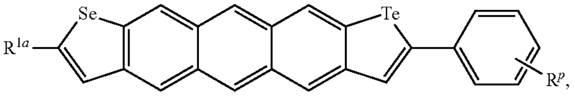

-continued
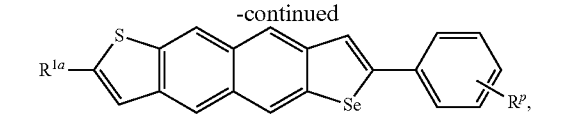
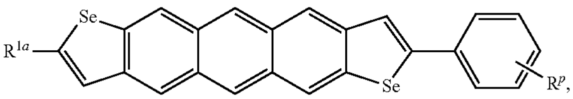
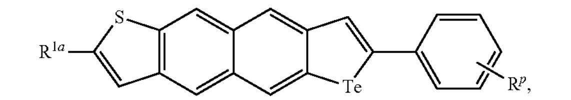
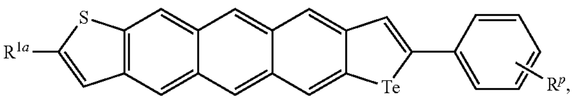
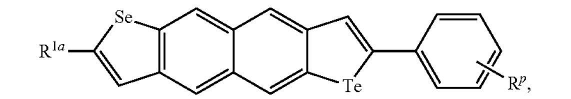
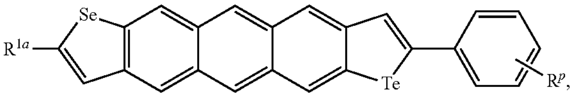
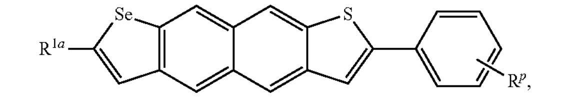
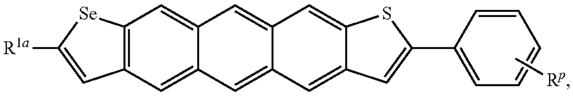
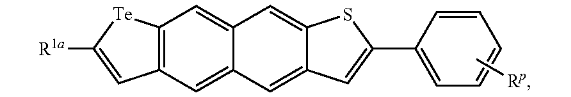
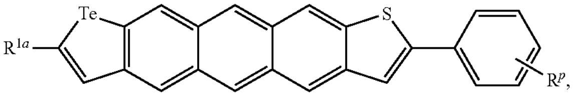
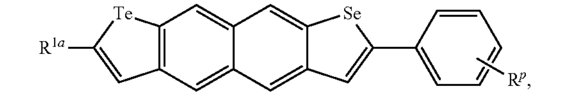
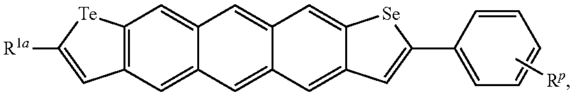
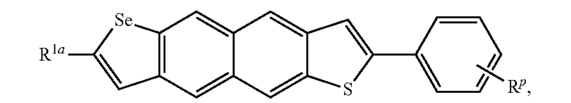
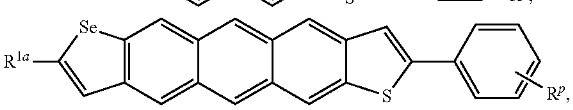
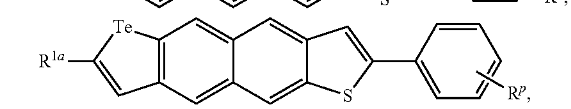
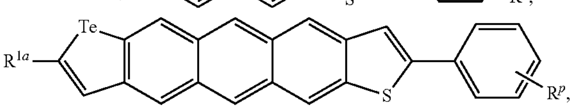
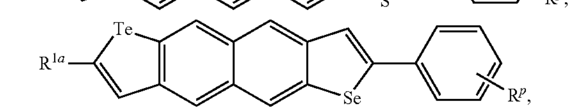
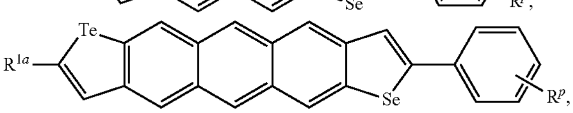
-continued
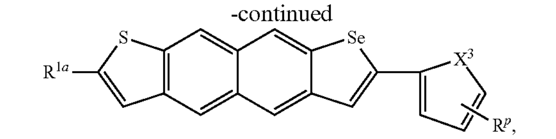
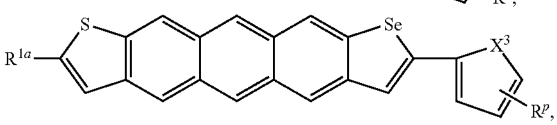
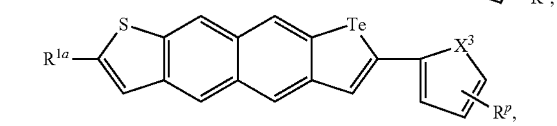
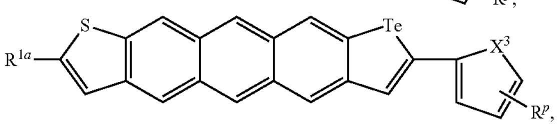
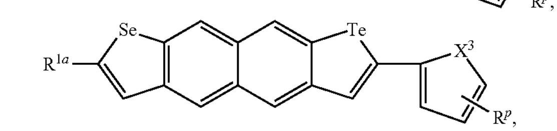
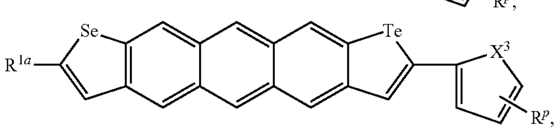
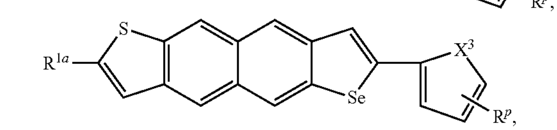
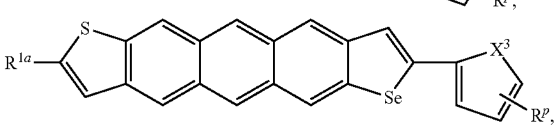
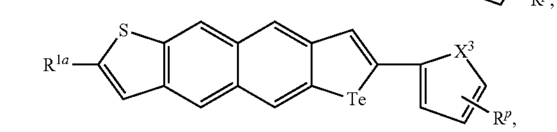
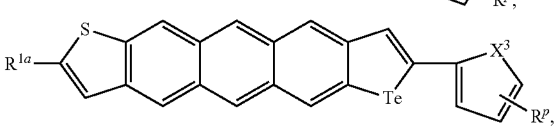
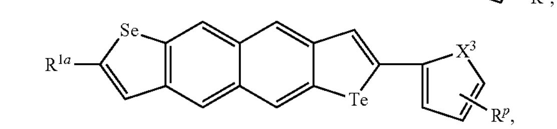
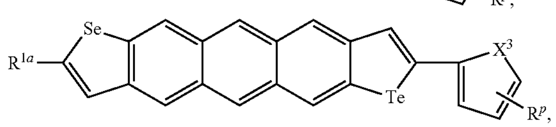
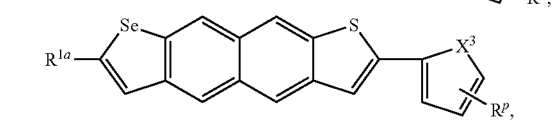
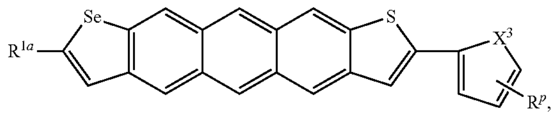
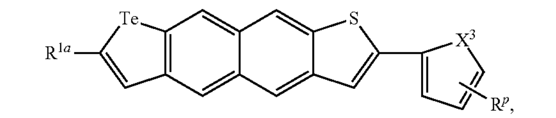

-continued
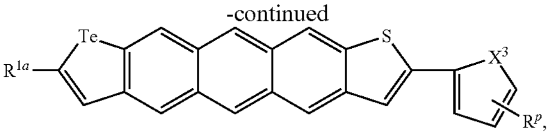
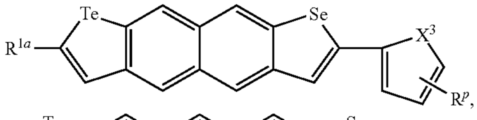
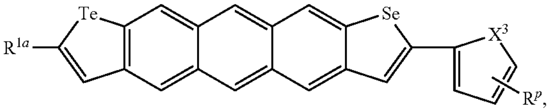
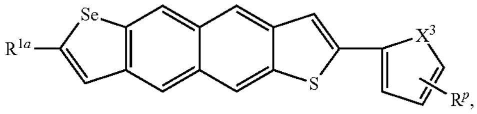
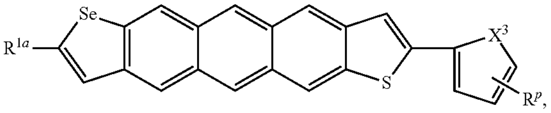
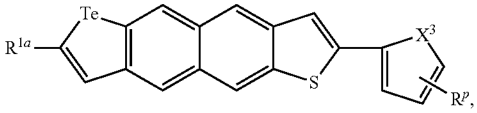
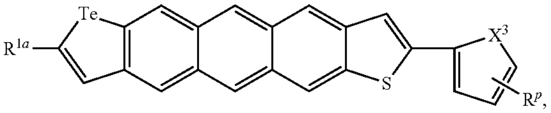
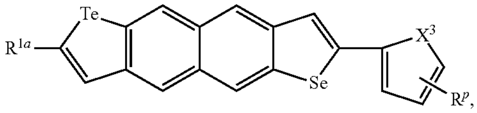
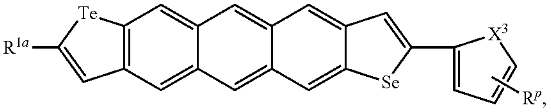
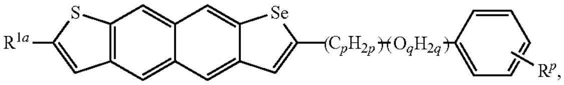
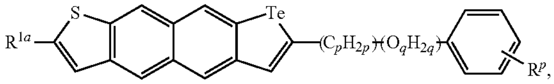
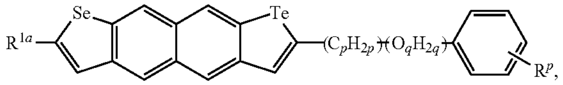
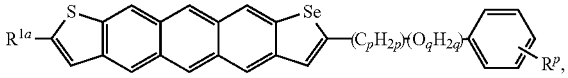
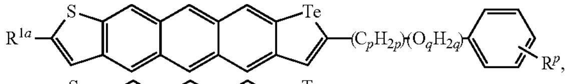
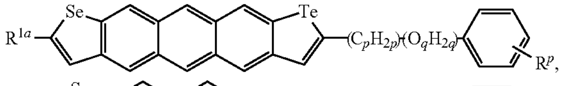
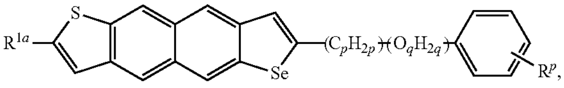
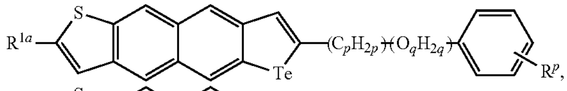
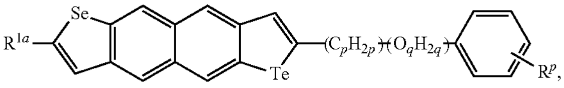
-continued
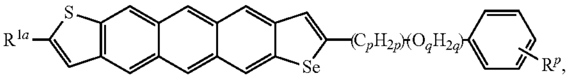
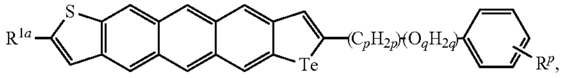
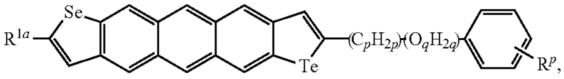
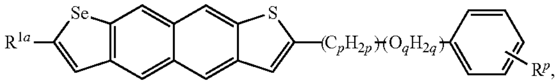
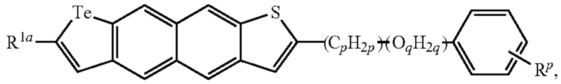
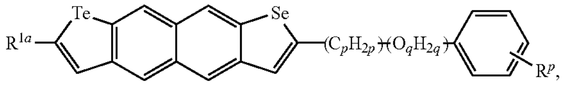
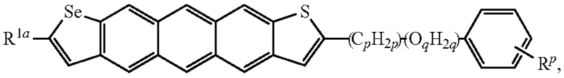
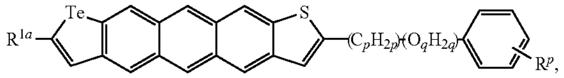
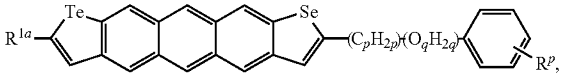
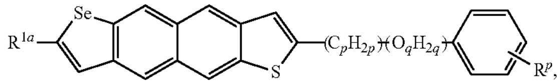
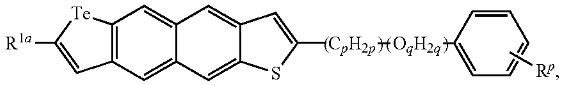
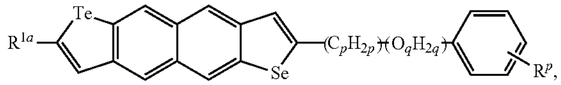
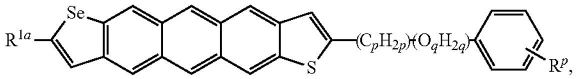
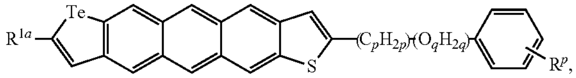
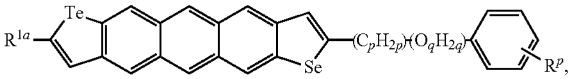
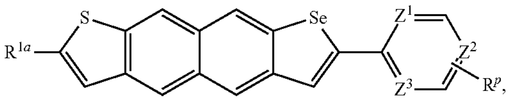
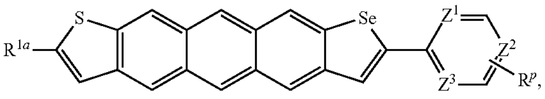
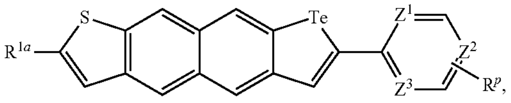
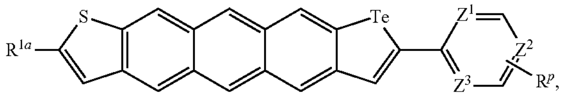
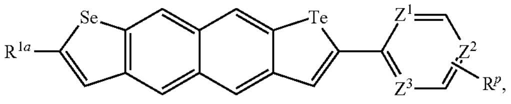

-continued

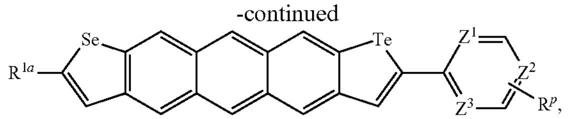

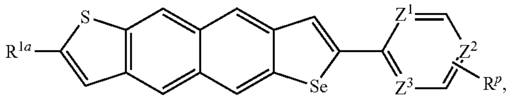

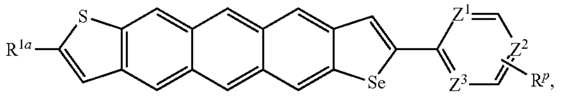

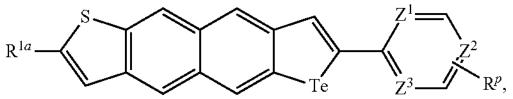

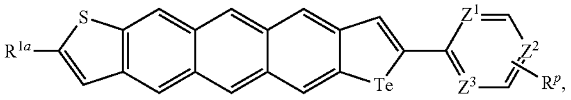

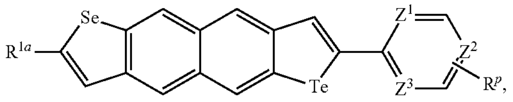

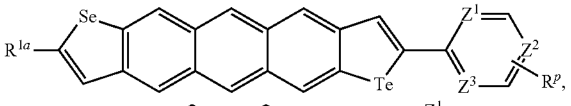

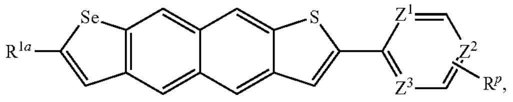

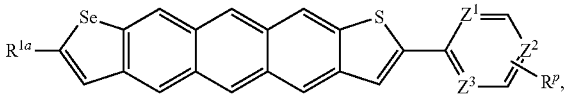

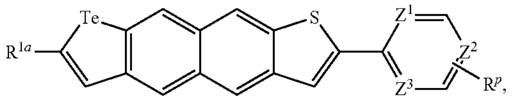

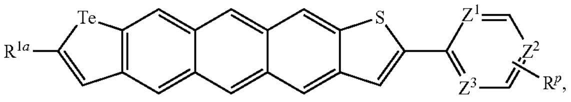

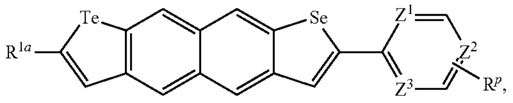

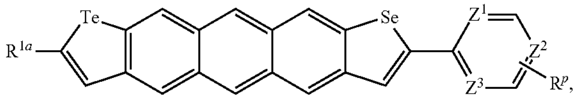

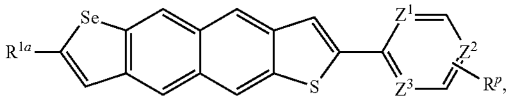

-continued

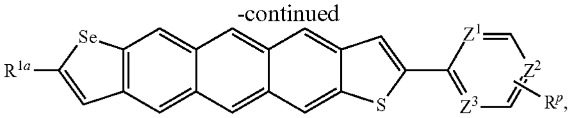

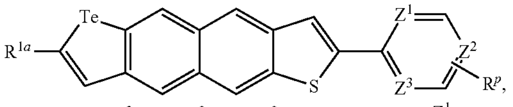

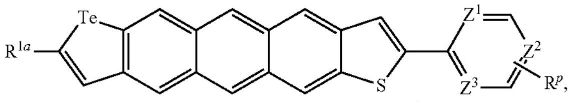

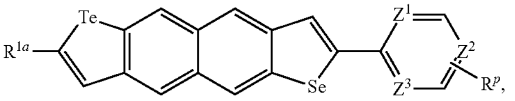

and

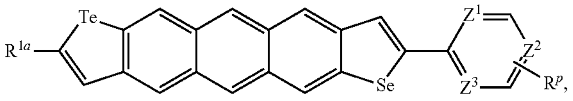

wherein, in Group 2, $R^{1a}$ is hydrogen or a substituted or unsubstituted C1 to C30 alkyl group, $Z^1$ to $Z^3$ are independently N or $CR^a$, provided that one of $Z^1$ to $Z^3$ is N, $X^3$ is one of O, S, Se, Te, $NR^b$, or $CR^cR^d$, p and q are independently an integer of 1 to 30, and $R^p$ and $R^a$ to $R^d$ are independently one of hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and substituted refers to replacement of hydrogen of a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group, a sulfonic acid group, a phosphoric acid group, a C1 to C20 alkyl group, a C2 to C20 alkenyl group, a C2 to C20 alkynyl group, a C6 to C30 aryl group, a C3 to C30 heteroaryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

12. An electronic device comprising the thin film transistor of claim 1.

* * * * *